(12) United States Patent
Mallett et al.

(10) Patent No.: US 11,675,034 B2
(45) Date of Patent: Jun. 13, 2023

(54) MAGNETIC RESONANCE SCANNER AND MAGNETIC RESONANCE IMAGING SYSTEM

(71) Applicant: Siemens Healthcare GmbH, Erlangen (DE)

(72) Inventors: Michael Mallett, Eynsham (GB); Stefan Popescu, Erlangen (DE); Adrian Mark Thomas, Eynsham (GB); Stephan Biber, Erlangen (DE); Matthias Gebhardt, Erlangen (DE); Thorsten Speckner, Erlangen (DE); Thomas Beck, Dormitz (DE); Andreas Greiser, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 96 days.

(21) Appl. No.: 17/306,149

(22) Filed: May 3, 2021

(65) Prior Publication Data
US 2021/0341556 A1 Nov. 4, 2021

Related U.S. Application Data

(60) Provisional application No. 63/019,691, filed on May 4, 2020.

(51) Int. Cl.
| | |
|---|---|
| *G01R 33/341* | (2006.01) |
| *H01Q 21/24* | (2006.01) |
| *G01R 33/383* | (2006.01) |
| *G01R 33/3815* | (2006.01) |
| *H01Q 7/00* | (2006.01) |
| *A61B 5/055* | (2006.01) |

(52) U.S. Cl.
CPC ........ *G01R 33/341* (2013.01); *G01R 33/383* (2013.01); *G01R 33/3815* (2013.01); *H01Q 7/00* (2013.01); *H01Q 21/24* (2013.01); *A61B 5/055* (2013.01)

(58) Field of Classification Search
None
See application file for complete search history.

(56) References Cited

U.S. PATENT DOCUMENTS

| | | | | |
|---|---|---|---|---|
| 4,985,678 A | * | 1/1991 | Gangarosa | A61B 5/055 324/318 |
| 5,305,749 A | * | 4/1994 | Li | A61B 5/055 324/318 |

(Continued)

FOREIGN PATENT DOCUMENTS

| | | |
|---|---|---|
| EP | 3828573 A1 | 6/2021 |
| EP | 3896473 A1 | 10/2021 |

*Primary Examiner* — Rodney E Fuller
(74) *Attorney, Agent, or Firm* — Harness, Dickey & Pierce, P.L.C.

(57) ABSTRACT

A magnetic resonance imaging system comprises a field generation unit and a supporting structure for providing structural support for the field generation unit, wherein the field generation unit comprises at least one magnet for generating a B0 magnetic field and an opening configured to provide access to an imaging volume positioned in the B0 magnetic field along at least one direction and wherein the at least one direction is angled with respect to a main direction of magnetic field lines of the B0 magnetic field in the imaging volume.

25 Claims, 20 Drawing Sheets

(56) References Cited

U.S. PATENT DOCUMENTS

| | | | | |
|---|---|---|---|---|
| 5,565,834 A | * | 10/1996 | Hanley | G01R 33/44 324/319 |
| 6,011,396 A | * | 1/2000 | Eckels | G01R 33/3806 324/309 |
| 6,317,618 B1 | * | 11/2001 | Livni | G01R 33/28 324/318 |
| 2002/0123681 A1 | * | 9/2002 | Zuk | A61B 5/055 600/410 |
| 2003/0001575 A1 | * | 1/2003 | Cheng | G01R 33/3806 324/318 |
| 2004/0135580 A1 | * | 7/2004 | Abele | G01R 33/3806 324/309 |
| 2010/0219833 A1 | * | 9/2010 | McGinley | G01R 33/383 324/318 |
| 2018/0199853 A1 | | 7/2018 | Abkai et al. | |
| 2019/0317168 A1 | | 10/2019 | Popescu | |
| 2019/0353726 A1 | * | 11/2019 | Poole | G01R 33/3802 |
| 2020/0025846 A1 | * | 1/2020 | Nelson | A61B 90/14 |
| 2020/0355771 A1 | | 11/2020 | Popescu et al. | |
| 2021/0015394 A1 | * | 1/2021 | Zhang | G01R 33/3806 |
| 2021/0156936 A1 | | 5/2021 | Popescu | |
| 2021/0156941 A1 | | 5/2021 | Popescu et al. | |
| 2021/0325493 A1 | | 10/2021 | Kirsch et al. | |
| 2022/0065961 A1 | | 3/2022 | Gebhardt et al. | |

\* cited by examiner

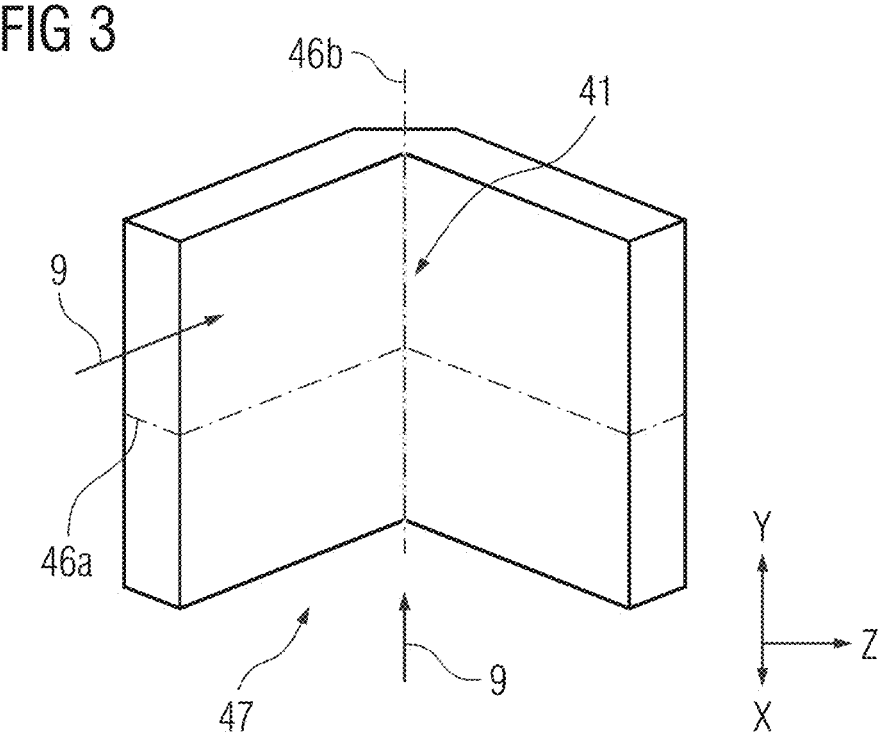

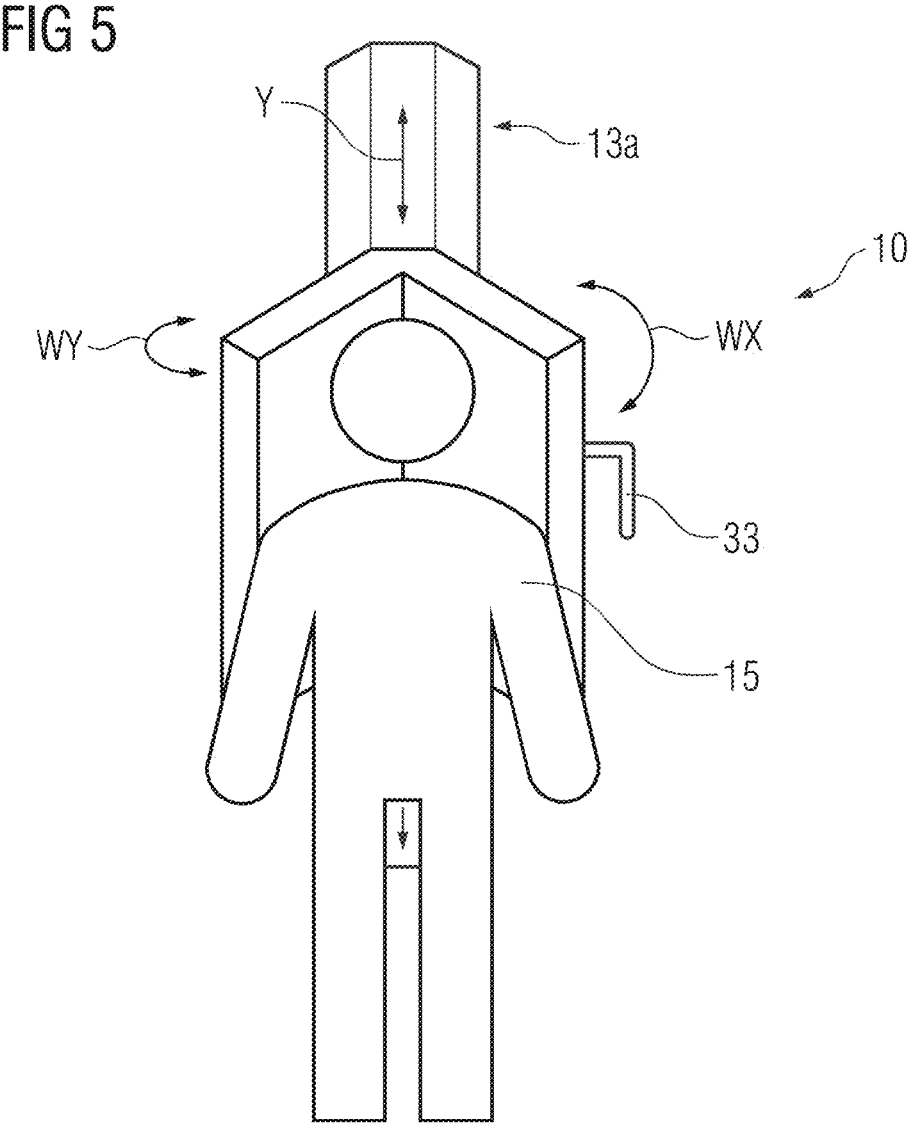

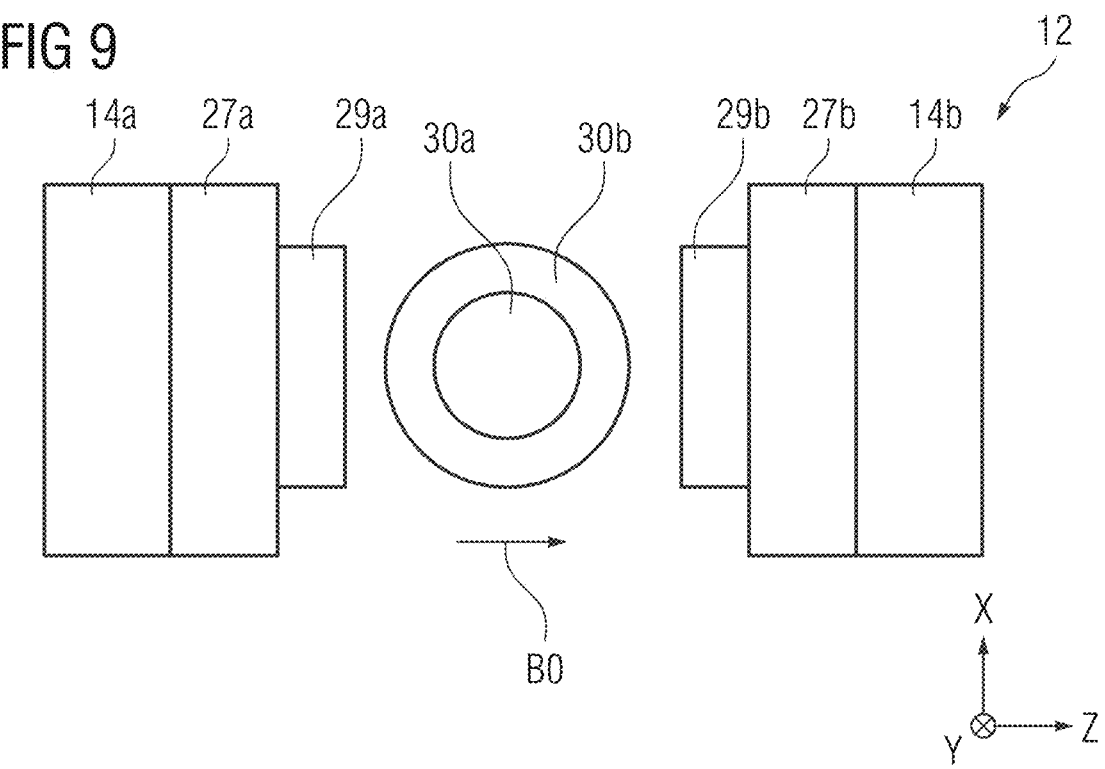

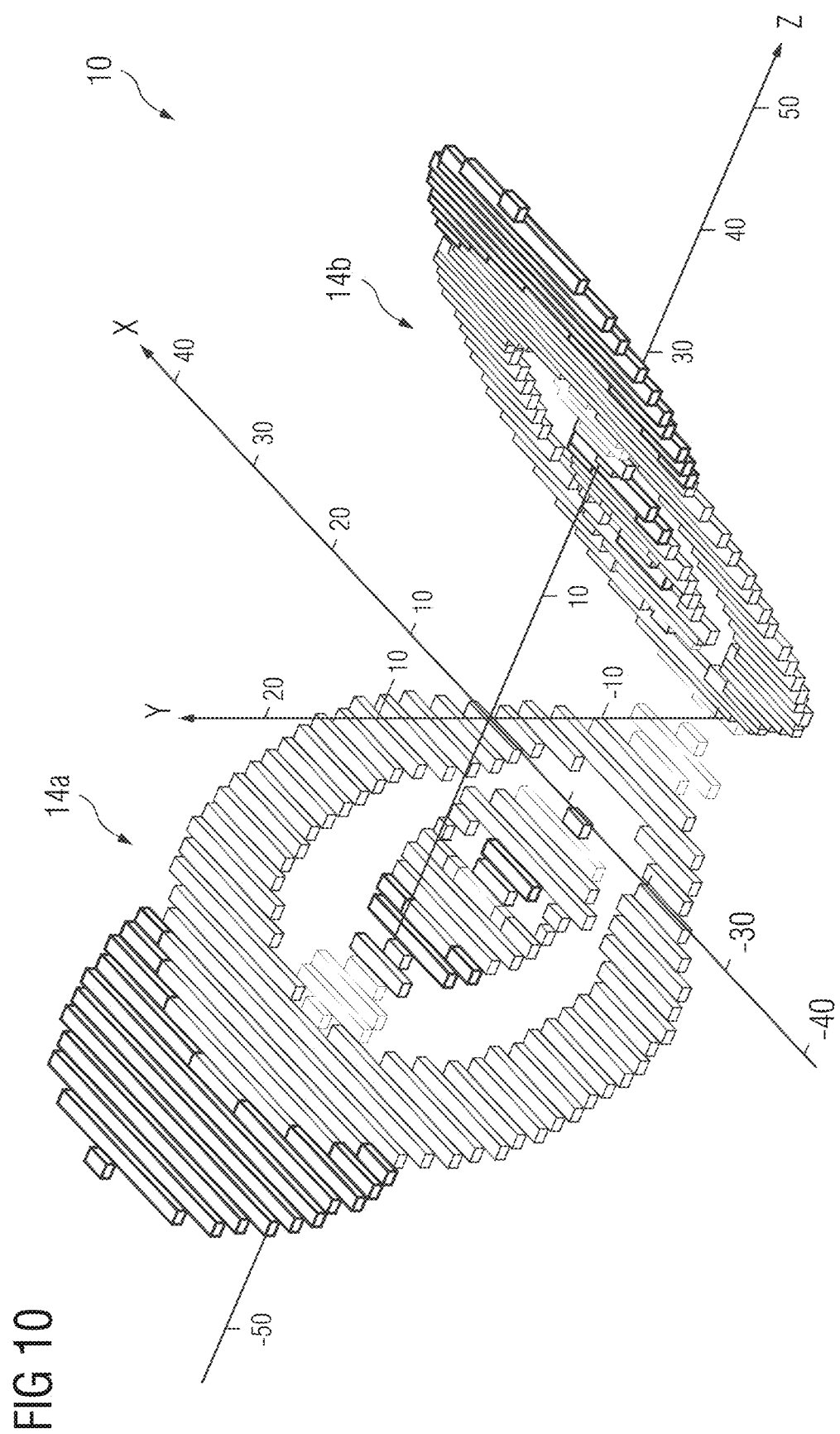

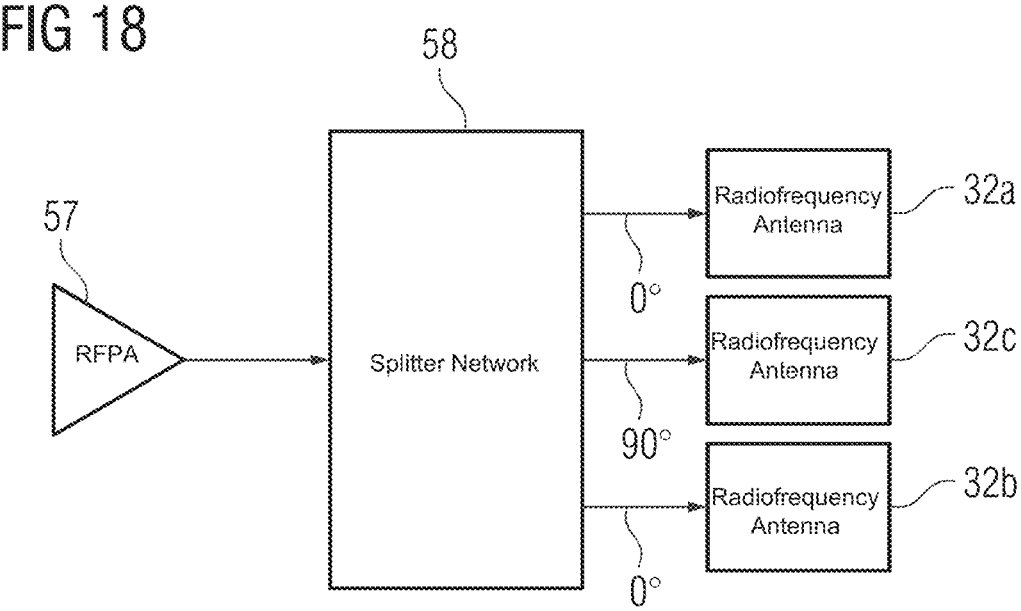

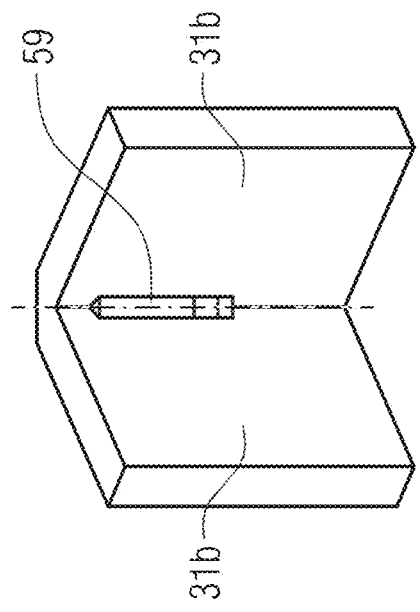
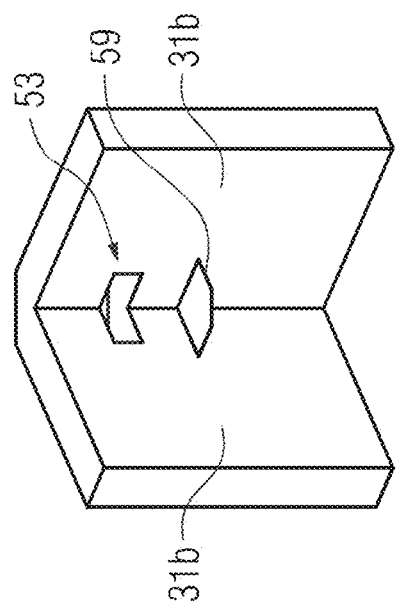
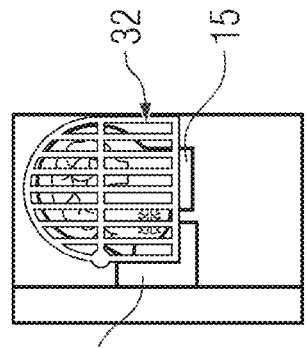
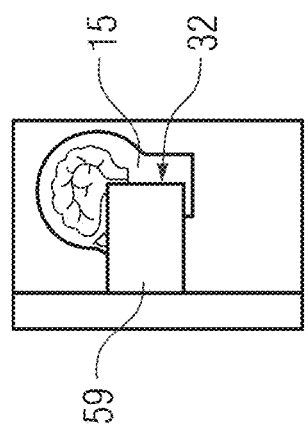
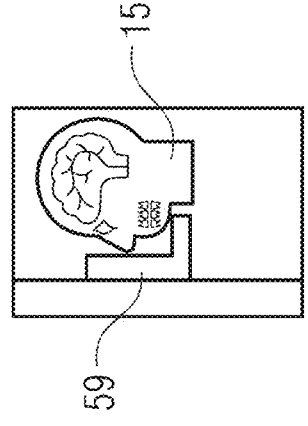

MAGNETIC RESONANCE SCANNER AND MAGNETIC RESONANCE IMAGING SYSTEM

PRIORITY STATEMENT

The present application hereby claims priority under 35 U.S.C. § 119(e) to U.S. provisional patent application No. 63/019,691 filed May 4, 2020, the entire contents of which are hereby incorporated herein by reference.

FIELD

At least some example embodiments generally relate to a magnetic resonance imaging system suitable for imaging of dedicated body or organ parts of a patient.

BACKGROUND

Magnetic resonance tomography represents a prominent imaging method for acquiring images of an interior of the examination object. For carrying out a magnetic resonance measurement, the examination object is usually positioned in a strong and homogeneous static magnetic field (B0 field) of a magnetic resonance imaging device. The static magnetic field may comprise magnetic field strengths of 0.2 Tesla to 7 Tesla, thus aligning nuclear spins inside the examination object along the static magnetic field. For triggering so-called nuclear spin resonances, radiofrequency excitation pulses are emitted into the examination subject. Each radiofrequency excitation pulse causes a magnetization of nuclear spins within the examination object to deviate from the static magnetic field by an amount which is known as the flip angle. A radiofrequency excitation pulse may comprise an alternating (electro-)magnetic field with a frequency which corresponds to the Larmor frequency at the respective static magnetic field strength. Excited nuclear spins may exhibit a rotating and decaying magnetization (nuclear magnetic resonance), which can be detected using dedicated radiofrequency antennas. For spatial encoding of measured data, rapidly switched magnetic gradient fields are superimposed on the static magnetic field.

The received nuclear magnetic resonances are typically digitized and stored as complex values in a k-space matrix. This k-space matrix can be used as a basis for a reconstruction of magnetic resonance images and for determining spectroscopic data. A magnetic resonance image is typically reconstructed using a multi-dimensional Fourier transformation of the k-space matrix.

SUMMARY

During an imaging examination, the patient is typically enclosed in a bore or between a pair of magnets of the magnetic resonance imaging device. Due to spatial restrictions within the bore or a space between the pair of magnets, magnetic resonance imaging provides limited support for surgical procedures or biopsies. As the patient needs to be positioned inside the magnetic resonance imaging device, a size of the bore as well as other dimensions of the magnetic resonance imaging device are dictated by the size of the human body. From a cost and/or space utilization perspective, this may be unsatisfactory, especially if the examination is restricted to a body region of the patient, which is significantly smaller than an imaging volume provided by the magnetic resonance imaging device. Furthermore, patients with a claustrophobic condition or children may not tolerate elongated examination times usually associated with a magnetic resonance measurement.

At least one example embodiment provides a magnetic resonance imaging system with enhanced openness and/or accessibility for imaging of dedicated body regions of a patient.

At least one example embodiment directed to a magnetic resonance imaging system comprising a field generation unit, a supporting structure for providing structural support for the field generation unit, a radiofrequency system comprising at least one radiofrequency antenna for transmitting and/or receiving radiofrequency radiation and a gradient field system comprising at least one gradient coil for generating at least one magnetic gradient field. The field generation unit comprises at least one magnet for generating a B0 magnetic field and an opening configured to provide access to an imaging volume positioned in the B0 magnetic field along a direction of access in a unilateral manner, wherein the direction of access to the imaging volume is angled with respect to a main direction of magnetic field lines of the B0 magnetic field in the imaging volume.

BRIEF DESCRIPTION OF THE DRAWINGS

Further advantages and details of example embodiments may be recognized from the embodiments described below as well as the drawings. The figures show:

FIG. 3 illustrates a schematic representation of an embodiment of a magnetic resonance imaging system, FIG. 5 illustrates a schematic representation of an embodiment of a magnetic resonance imaging system, FIG. 9 illustrates a schematic representation of an embodiment of a field generation unit of a magnetic resonance imaging system, FIG. 10 illustrates a representation of an embodiment of a magnetic resonance imaging system, FIG. 18 illustrates a schematic representation of an embodiment of a radiofrequency system of a magnetic resonance imaging system, FIGS. 19a-19e illustrate a schematic representation of embodiments of a magnetic resonance imaging system.

DETAILED DESCRIPTION OF EXAMPLE EMBODIMENTS

Figure 1:
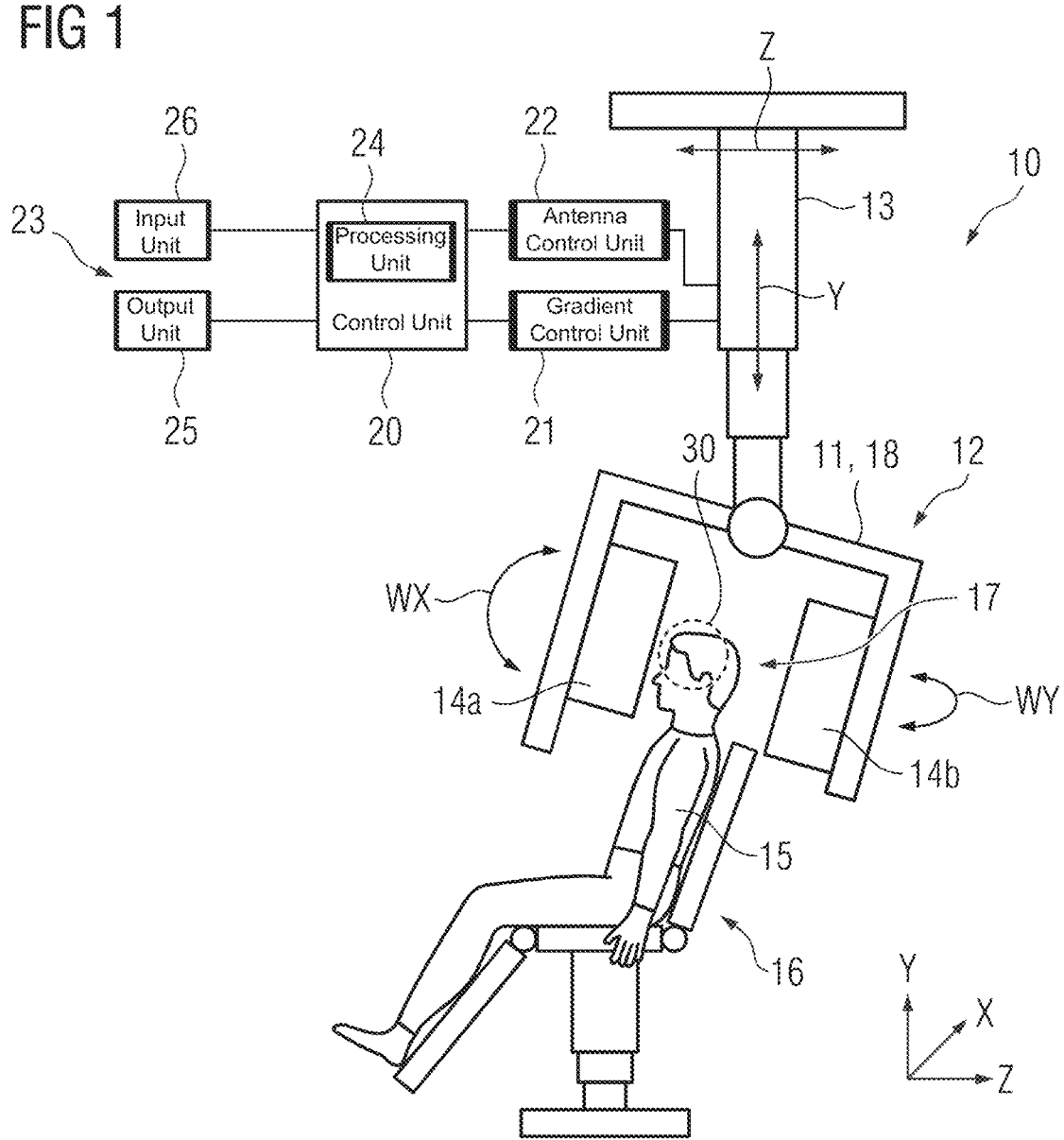
FIG. 1 illustrates a schematic representation of an embodiment of a magnetic resonance imaging system.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing at least some example embodiments. Example embodiments may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment of the invention relates to the non-transitory computer-readable storage medium including electronically readable control information (processor executable instructions) stored thereon, configured in such that when the storage medium is used in a controller of a device, at least one embodiment may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

The apparatuses and methods described in this application may implemented using a special purpose computer created by configuring a general purpose computer to execute one or more particular functions embodied in computer programs.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one example embodiment is directed to a magnetic resonance imaging system comprising a field generation unit, a supporting structure for providing structural support for the field generation unit, a radiofrequency system comprising at least one radiofrequency antenna for transmitting and/or receiving radiofrequency radiation and a gradient field system comprising at least one gradient coil for generating at least one magnetic gradient field. The field generation unit comprises at least one magnet for generating a B0 magnetic field and an opening configured to provide access to an imaging volume positioned in the B0 magnetic field along a direction of access in a unilateral manner, wherein the direction of access to the imaging volume is angled with respect to a main direction of magnetic field lines of the B0 magnetic field in the imaging volume.

A supporting structure may be configured to adjust a position and/or an orientation of the field generation unit and/or to align the at least one magnet with an examination object. In one example, the supporting structure may comprise a positioning unit, such as a swivel joint, a rotating joint or the like. The positioning unit may be configured to adjust a position and/or an orientation of the field generation unit with respect to the examination object. In another example, the positioning unit may comprise a telescope system and/or a rail system configured to adjust a height and/or a distance of the field generation unit with respect to the examination object. The supporting structure and/or the positioning unit may allow movement of the field generation unit and/or the magnetic resonance imaging system along at least two spatial directions, at least three spatial directions, at least four spatial directions or at least five spatial directions. Particularly, the supporting structure and/or the positioning unit may enable adjusting a position and/or an orientation of the field generation unit and/or the magnetic resonance imaging system in a three-dimensional space.

The supporting structure may further be configured to maintain a relative position between the at least one magnet and a second magnet of the field generation unit. The supporting structure may be comprised of any material as well as compounds, composites, alloys or combinations of materials, that are able to withstand the gravitational, magnetic and/or mechanical forces exerted on or by the at least one magnet and/or the field generation unit. Typical examples of suitable materials are metals, alloys, ceramics, as well as natural and synthetic materials. In particular, the supporting structure may comprise a yoke. The yoke may enhance, enforce and/or restrict a magnetic flux density in specific regions of the magnetic resonance imaging system, such as a half-open space and/or the imaging volume. In at least one example embodiment, the yoke is made of a material with high magnetic permeability. Particularly, the yoke may comprise a high amount of iron and/or other ferromagnetic materials. For example, the yoke may comprise more than 98% or more than 99% iron. In one embodiment, the yoke may contain 1006 carbon steel according to the definition of the American Iron and Steel Institute (AISI). Furthermore, the supporting structure may comprise other materials with high magnetic permeability, such as Fe, Nd or alloys of Fe, Nd and other elements enhancing a magnetic flux. The supporting structure and/or yoke may be designed to enhance, restrict or shape the magnetic field of the field generation unit. In at least one example embodiment, the magnetic field is purposefully modified by adjusting movable parts of the supporting structure, the yoke and/or the field generation unit. In one embodiment, the supporting structure may comprise an overall shape of a triangle, an 'L', a 'V', a 'U' or a 'Bell'.

The at least one magnet of the field generation unit may be configured to provide a static magnetic field (B0 magnetic field) in the imaging volume over a predetermined time period. In one embodiment, the magnetic field provided by the at least one magnet may be constant over a time period of a few milliseconds to a few seconds. In another embodiment, the magnetic field provided by the at least one magnet may be constant over a time period of several days, several months or several years.

The field generation unit may comprise at least one magnet confining the imaging volume from at least one spatial direction. The field generation unit may also comprise at least two magnets, confining the imaging volume from at least two spatial directions. For example, the at least one magnet of the field generation unit may confine the imaging volume from a first spatial direction and the second magnet may confine the imaging volume from a second spatial direction different from the first spatial direction. The first spatial direction and the second spatial direction may be oriented in a parallel manner. In at least one example embodiment, the field generation unit comprises a plurality of connected or separated magnet sections. The magnet sections may be arranged in different positions and/or in different orientations with respect to the imaging volume.

The field generation may comprise a half-open space, confined by the at least one magnet in at least one spatial direction. The half-open space may also be confined by the at least one magnet and the second magnet of the field generation unit in at least the first spatial direction and the second spatial direction. However, the half-open space may also be confined by the field generation unit in at least three spatial directions. For example, the half-open space may be confined by the supporting structure in a third spatial direction. In an example embodiment, the half-open space provides access to the imaging volume in two essentially perpendicular spatial directions. The half-open space may represent a volume wherein the examination object is positioned for performing a magnetic resonance imaging examination. The opening configured to provide access to the imaging volume may also provide access to the half-open space. The opening may be characterized by an aperture, a pathway, a passage or a free volume, which provides an unobstructed entrance to the imaging volume from a surrounding environment (e. g. an examination room). The opening may comprise any shape or geometry suitable for receiving or accommodating an examination object. In an embodiment, a geometry of the at least one magnet, the field generation unit and/or the opening is configured to provide enhanced accessibility of a patient and/or a specific body region of the patient to the imaging volume. Furthermore, a shape of the field generation unit and/or the supporting structure may be designed in consideration of a superposition of sizes and orientations of relevant anatomies to be covered andan orientation, a shape and/or a size of the imaging volume in the half-open space and removing constraints to provide sufficient patient access.

According to at least one example embodiment, the opening of the magnetic resonance system may provide an access to an imaging volume positioned in the B0 magnetic field along at least one spatial direction, wherein the at least one spatial direction is angled with respect to a main direction of magnetic field lines of the B0 magnetic field in the imaging volume. For example, the opening may provide an easy patient access along a direction of access in a unilateral manner. The opening of the field generation unit may be large enough to allow for insertion of a target anatomy, but still provide sufficient coverage of the subject to generate an appropriate B0 magnetic field for magnetic resonance imaging examinations. In an example embodiment, the direction of access to the imaging volume is angled with respect to a main direction of magnetic field lines of the B0 magnetic field in the imaging volume. In a further embodiment, the opening is configured to provide access to an imaging volume positioned in the B0 magnetic field along at least two perpendicular spatial directions. In this case, each of the at least two perpendicular spatial directions is angled with respect to a main direction of magnetic field lines of the B0 magnetic field in the imaging volume.

The imaging volume may be characterized by a particularly homogenous magnetic field. However, in at least one example embodiment, the imaging volume is characterized by an approximately linear magnetic field gradient. A size of the imaging volume may coincide with a size of the magnetic field provided by the at least one magnet. However, the size of the imaging volume may also be significantly smaller than the size of the magnetic field. The imaging volume may comprise an isocenter. An isocenter may represent a volume wherein the magnetic field provided by the at least one magnet is particularly homogenous.

A shape of the imaging volume may be characterized by a predefined variability of the B0 magnetic field. As a property of the B0 magnetic field may significantly be affected by an arrangement and/or a design of the field generation unit, the shape of the imaging volume may depend for instance a type, a material, as well as an angle and/or a distance between magnets and/or magnet sections in the field generation unit. In at least one example embodiment, such a dependency is exploited to match the shape of the imaging volume to specific imaging applications.

In one embodiment, the magnetic resonance imaging system provides a small, targeted imaging volume specifically adapted for imaging of a specific body region of the patient in order to reduce an overall size of the at least one magnet. The imaging volume of the magnetic resonance imaging system may be substantially smaller than a conventional imaging volume of a radiological magnetic resonance imaging system. For example, a maximum diameter of a sphere with the same volume as the imaging volume (diameter of spherical volume—DSV) is smaller than 25 cm, smaller than 20 cm, smaller than 15 cm, smaller than 10 cm, smaller than 8 cm, smaller than 6 cm, or smaller than 5 cm. A minimum dimension of an essentially homogeneous volume within the imaging volume may be 2 cm, or 5 cm, or 8 cm, or 10 cm, with a spherical or non-spherical shape, e. g. an ellipsoidal shape, a conical shape, a toroidal shape, a cuboid shape or any shape obtained by twisting and/or deforming of one of those shapes.

The gradient field system may comprise one or more gradient coils, which provide a magnetic gradient field varying along an x-direction, a y-direction and/or a z-direction. In one embodiment, the at least one gradient coil may comprise a coil of wire, which generates a magnetic field when a current is applied. In at least one example embodiment, the gradient field system is carried by the supporting structure and/or the at least one magnet. For example, the at least one gradient coil may be positioned as an additional layer adjacent to the at least one magnet of the field generation unit. Particularly, the at least one gradient coil may be at least partially recessed into a pole face of the at least one magnet. In at least one example embodiment, a value for the maximum gradient field strength provided via the gradient field system may range between 10 and 30 mT/m and a slew rate may range between 10 and 30 T/m/s. However, this range can also be upwardly or downwardly transgressed on a case-by-case basis.

The radiofrequency system may comprise one or more radiofrequency antennas for transmitting radiofrequency excitation pulses and/or receiving magnetic resonance signals. In at least one example embodiment, the radiofrequency system comprises at least two radiofrequency antennas. The at least two radiofrequency antennas may be positioned at two opposing sides of the field generation unit. In at least one example embodiment, at least one radiofrequency antenna is carried by the supporting structure and/or the at least one magnet. The radiofrequency system may be designed to match a contour and/or a surface of the imaging object in order to increase coverage of the imaging object and/or decrease a distance between a radiofrequency antenna and the surface of the imaging object. However, the at least one radiofrequency antenna may also be shaped to match a surface of a pole face of the at least one magnet.

According to one embodiment, the field generation unit may provide an access to the imaging volume along at least two perpendicular spatial directions. For example, a direction of access may be provided along at least two axes of a cartesian coordinate system, wherein a coordinate origin of the cartesian coordinate system may be positioned at a center of the imaging volume. However, the field generation may also be configured to provide an access to the imaging volume along three perpendicular spatial directions.

An angle between the direction of access to the imaging volume and the main direction of the magnetic field lines of the B0 magnetic field may be different from zero and different from 180°. In case the imaging volume may be accessed from two or more perpendicular spatial directions, each of the two or more directions of access may be angled with respect to the main direction of magnetic field lines of the B0 magnetic field. Likewise, the angle between the at least one spatial direction or the at least two spatial directions and the main direction of the magnetic field lines of the B0 magnetic field may be different from zero and different from 180°. For example, the angle may range between 10° and 170°, 20° and 160°, 30 and 150° degrees, 40 and 140°. In one embodiment, the at least one spatial direction or the at least two perpendicular spatial directions may be oriented essentially perpendicular with respect to the main direction of magnetic field lines of the B0 magnetic field in the imaging volume.

The magnetic resonance imaging system may be configured to acquire magnetic resonance imaging data from an examination object positioned in the half-open space. For this purpose, the magnetic resonance imaging system may comprise further components usually required for performing a magnetic resonance imaging examination and for processing acquired magnetic resonance imaging data. In particular, the magnetic resonance imaging system may comprise a processing unit which may be configured to reconstruct a magnetic resonance image from magnetic resonance signals acquired from the image acquisition region.

The magnetic resonance imaging system may be a dedicated scanner configured to perform a magnetic resonance imaging examination of a specific body region or a plurality of specific body regions of a patient. For example, a specific body region may comprise a heart, an eye, a tooth, multiple teeth, a jaw region, a prostate, and the like.

In one embodiment, a restriction or containment of the magnetic field, particularly a stray magnetic field, is realized via implementation of a yoke. In another embodiment, the restriction of the magnetic field is realized via active shielding for stray field reduction. In at least one example embodiment, both measures are combined to provide a restriction of the magnetic field.

The magnetic resonance imaging system according to at least one example embodiment may be used as a dedicated scanner for one or more specific body regions of a patient. Thus, an overall dimension of the magnetic resonance imaging system may favorably be reduced in comparison to conventional, hole-body magnetic resonance imaging systems. Furthermore, smaller magnetic resonance imaging systems may be less expensive and/or easier to install in confined spaces in comparison to conventional magnetic resonance imaging systems.

In providing a field generation unit according to an embodiment of the magnetic resonance imaging system, the imaging volume may favorably be accessible for a plurality of anatomic regions, such as the head, the extremities and the prostate.

The magnetic resonance imaging system may allow for imaging of the patient in different positions and/or postures (e.g. in standing, sitting or in lying positions). Thus, surgery and/or therapy may favorably be performed during an imaging examination. Furthermore, vertebrae of the patient may advantageously be imaged in a standing position.

Due to an enhanced accessibility and/or openness, the magnetic resonance imaging system according to at least some example embodiments may easily be combined with other imaging modalities, such as a flatbed or C-arm X-ray scanner, an ultrasound scanner, as well as optical imaging devices. Particularly, other imaging modalities may favorably provide high resolution localizer data which may be used to improve an efficiency of an imaging examination as well as a quality of acquired magnetic resonance images.

As a further advantage, an obstruction of a view of the patient by a bore or a field generation unit of the magnetic resonance imaging system can significantly be reduced in comparison to conventional magnetic resonance imaging systems. Thus, abortions of a magnetic resonance imaging examination of claustrophobic patients may favorably be reduced and an eye-contact between parents and children can be maintained during an imaging examination.

Due to a reduced dimension of the magnetic resonance imaging system in comparison to conventional magnetic resonance imaging systems, a mobile version of the magnetic resonance imaging system may be provided. A mobile version may especially be beneficial for interventional applications both in an operating room or outside a hospital building. For example, field hospitals in battle zones may favorably benefit from a facilitated patient access due to the openness of the magnetic resonance imaging system.

With such a magnetic resonance imaging system, all advantages of a homogenous magnetic field would apply and known types of imaging sequences may be operated.

According to an embodiment of the magnetic resonance imaging system, the field generation unit is configured to at least partially encompass the imaging volume in such a way, that a free volume is encompassed by the field generation unit, wherein a ratio of the volume of the imaging volume and the free volume partially encompassed by the field generation unit ranges between 0.05 and 1.

In a further embodiment of the magnetic resonance imaging system, the at least one magnet comprises a permanent magnet or an array of permanent magnets.

A permanent magnet may consist of any suitable magnetic material such as AlNiCo (aluminum-nickel-cobalt), NeFeB (neodymium-iron-boron) or SmCo (samarium-cobalt) alloys. Furthermore, the permanent magnet may comprise any desired shape. In one embodiment, the permanent magnet comprises a bar shape. A bar shape may include a cuboid bar shape, a cylindrical bar shape or a bar shape with a polygonal cross-section, such as a prism. Bar-shaped permanent magnets provide a low-cost solution for generating a magnetic field within the imaging volume. In another embodiment, the permanent magnet may be composed of smaller, stacked permanent magnets or an array of permanent magnets. An array of permanent magnets may be a Hallbach array. The use of a permanent magnet may favorably avoid costs and space required for cooling equipment usually associated with superconducting magnets and electromagnets.

However, the at least one magnet of the field generation unit may also comprise an electromagnet. An electromagnet may be a non-superconducting magnet. Particularly, an electromagnet may comprise an electrical conductor wound around a magnetic core made of, for example, a ferromagnetic or ferrimagnetic material. The magnetic core of the electromagnet may comprise a cylindrical shape, a cuboid shape, a prism shape or any other desirable shape. By using an electromagnet, the magnetic field strength can be favorably increased in comparison to a permanent magnet of comparable size. Higher magnetic field strengths can advantageously enhance a quality and/or a signal-to-noise ratio of a magnetic resonance image acquired via the magnetic resonance imaging system.

According to a further embodiment of the magnetic resonance imaging system, the at least one magnet comprises high temperature superconducting materials and/or low temperature superconducting materials.

A superconducting magnet may comprise coils and/or tubular segments of superconducting wire. The superconducting wire may be connected to a cryostat to keep a temperature of the superconducting wire below a predefined value. In one example, liquid helium may be used as a coolant, ensuring a temperature of the superconducting wire below 4 K. The coils of superconducting wire may be arranged in a variety of shapes, such as a solenoid or as substantially planar loop or tubular segment. By using a superconducting magnet, the magnetic field strength can favorably be increased in comparison to a permanent magnet or an electromagnet of comparable size.

In a further embodiment of the magnetic resonance imaging system, the supporting structure is movably mounted and/or comprises movable parts to adjust a position of the field generating unit with respect to an imaging object and/or facilitate the access to the imaging volume. Particularly, the supporting may comprise and/or be attached to the positioning unit according to an embodiment described above.

In one embodiment of the magnetic resonance imaging system, a shape of the supporting structure is designed to match a contour and/or a surface of the imaging object to enhance coverage of the imaging object.

In a further embodiment of the magnetic resonance imaging system, the radiofrequency system is designed to match the contour and/or the surface of the imaging object to enhance coverage of the imaging object and/or decrease a distance between a radiofrequency antenna and the surface of the imaging object.

According to a further embodiment of the magnetic resonance imaging system, the field generation unit is designed to match at least a part of the contour and/or the surface of the imaging object to provide enhanced coverage of the imaging object.

In providing a supporting structure and/or a field generation unit which is matched with a contour and/or a surface of the imaging object, the at least one magnet, the at least one gradient coil and/or the at least one radiofrequency antenna may favorably be positioned in a close proximity to a target anatomy of the patient. Thus, a quality (e.g. a signal-to-noise ratio) of an acquired magnetic resonance may favorably be enhanced.

According to one embodiment of the magnetic resonance imaging system, the gradient field system comprises two gradient coils generating magnetic field gradients in a first direction and in a second direction oriented perpendicular to the first direction, wherein a spatial encoding in a third direction oriented perpendicular to the first direction and the second direction is accomplished via a static field gradient implemented by the B0 magnetic field. In providing a B0 magnetic field with a static field gradient, a third gradient coil may favorably be omitted. Thus, a number of components of the magnetic resonance imaging system may favorably be reduced in proximity to the imaging volume and an openness and/or an accessibility of the imaging volume may favorably be enhanced.

In one embodiment of the magnetic resonance imaging system, the field generation unit comprises at least one symmetry plane and the direction of access to the imaging volume is oriented perpendicular to the main direction of magnetic field lines of the B0 magnetic field and parallel to a symmetry plane of the field generation unit. In a further embodiment, the field generation unit comprises two symmetry planes.

According to a further embodiment of the magnetic resonance imaging system, a shape of the field generation unit is homeomorphic to a half-torus which is cut along a poloidal plane, wherein the opening is provided by the cut along the poloidal plane of the half-torus.

In one embodiment of the magnetic resonance imaging system, a cross-section of the field generation unit and/or the supporting structure comprises one of a 'U', a 'C', or a bell shape. In providing a field generation unit with one of the mentioned shapes, the accessibility of the magnetic resonance imaging system may advantageously be increased without compromising a sufficient enclosure of the target anatomy in the field generation unit and/or an efficiency of the field generation unit.

According to a further embodiment of the magnetic resonance imaging system, the field generation unit comprises at least two magnet sections, which are arranged at an angle towards each other, forming an essentially triangular half-open space enclosing at least a part of the imaging volume, wherein the opening is provided by the half-open space between the at least two magnet sections. In an example embodiment, the half-open space between the at least two magnet sections of the field generation unit provides access to the imaging volume in two essentially perpendicular spatial directions. In a further embodiment, the angle at which the at least two magnet sections are arranged comprises a value between 10 degrees and 180 degrees, preferably 60 and 120 degrees. In providing a field generation with a triangular or 'V'-shape, the accessibility of the imaging volume may favorably be improved with minimal impact on the efficiency of the field generation unit.

In one embodiment of the magnetic resonance imaging system, the supporting structure comprises two ending plates carrying the at least two magnet sections, wherein the ending plates are arranged in accordance with the essentially triangular half-open space comprising the imaging volume. An ending plate may be a separate piece or element mounted to the supporting structure. However, an ending plate may also be a part of the supporting structure.

According to a further embodiment of the magnetic resonance imaging system, the at least one gradient coil of the gradient field system is at least partially recessed into at least one of the at least two magnet sections.

In a further embodiment of the magnetic resonance imaging system, the radiofrequency system comprises at least two radiofrequency antennas, wherein at least one radiofrequency antenna is carried by either one of the ending plates. In providing a supporting structure and/or field generation unit which is matched to a contour and/or a surface of a target anatomy of the patient, the at least one radiofrequency antenna may favorably be located in close proximity to the target anatomy of the patient during an imaging examination. Thus, a signal-to-noise ratio of acquired magnetic resonance signals from the target anatomy may advantageously be improved.

According to an embodiment of the magnetic resonance imaging system, at least one radiofrequency antenna comprises a 90° phase shift of radiofrequency currents with respect to another radiofrequency antenna. In a further embodiment, the at least one radiofrequency antenna comprising a 90° phase shift of radiofrequency currents with respect to another radiofrequency antenna may be third radiofrequency antenna, which is positioned in a corner of the essentially triangular half-open space between the ending plates of the supporting structure. Using at least one radiofrequency antenna with a 90° phase shift of radiofrequency currents with respect to another radiofrequency antenna may favorably account for a triangular arrangement of radiofrequency antenna in a triangular field generation unit.

In yet another embodiment of the magnetic resonance imaging system, an amplitude of each radiofrequency antenna for transmitting is weighted by a splitter network to generate a homogenous and circularly polarized B1 magnetic field and/or a linearly polarized B1 magnetic field.

In a further embodiment of the magnetic resonance imaging system, at least one radiofrequency antenna comprises a coil of wire, wherein the coil of wire comprises a lemniscate shape, an oval shape, a polygonal shape, a shape comprising a plurality of polygons and/or ovals, or a shape obtained by twisting and/or distorting a polygon or an oval. For example, the shape of the imaging volume may be ellipsoidal, conical, toroidal or cuboid. The shape of the imaging volume may favorably correspond to a shape of a target anatomy. Thus, an acquisition of magnetic resonance signals from irrelevant body regions can advantageously be reduced and an efficiency of the magnetic resonance imaging examination can be increased. Furthermore, in omitting a requirement of a spherical imaging volume, an arrangement of one or more magnets of the field generation unit may favorably be optimized with respect to accessibility of the imaging volume and efficiency of the field generation unit. An efficiency of the field generation unit may relate to a weight and/or a volume of the field generation unit in relation to a provided magnetic field strength and/or magnetic field homogeneity.

According to a further embodiment of the magnetic resonance imaging system, the shape of the imaging volume is characterized by a predefined variability of the B0 magnetic field and the variability of the B0 magnetic field is disposed in a way, that the shape of the imaging volume is essentially non-spherical.

In one embodiment of the magnetic resonance imaging system, a minimum diameter of a sphere with a same volume as the imaging volume is in the range of 2 cm to 10 cm. In at least one example embodiment, a maximum diameter of the sphere with the same volume as the imaging volume is in the range of 10 cm to 25 cm. Preferably, the maximum diameter of the sphere with a same volume as the imaging volume is around 15 cm. In providing a small imaging volume in comparison to conventional magnetic resonance imaging system, a more space-efficient and/or cost-efficient magnetic resonance imaging system suitable for imaging of dedicated body regions of a patient may be provided.

According to an embodiment the magnetic resonance imaging system is configured to perform pre-polarization magnetic resonance imaging. In one example a stronger, but less homogeneous polarization field, e. g. an electro-magnet, is used to generate a high level of magnetization. For signal detection, a weaker, but more homogeneous field may be utilized.

Example embodiments of the magnetic resonance imaging system may be as follows:

In at least one example embodiment, a magnetic resonance imaging system comprising a field generation unit, a supporting structure for providing structural support for the field generation unit, a radiofrequency system comprising at least one radiofrequency antenna for transmitting and/or receiving radiofrequency radiation and a gradient field system comprising at least one gradient coil for generating at least one magnetic gradient field, wherein the field generation unit comprises at least one magnet for generating a B0 magnetic field and an opening configured to provide access to an imaging volume positioned in the B0 magnetic field along a direction of access in a unilateral manner, and wherein the direction of access to the imaging volume is angled with respect to a main direction of magnetic field lines of the B0 magnetic field in the imaging volume.

In at least one example embodiment, the field generation unit is configured to at least partially encompass the imaging volume in such a way that a free volume is encompassed by the field generation unit.

In at least one example embodiment, the ratio of the volume of the imaging volume to the free volume partially encompassed by the field generation unit ranges between 0.05 and 1.

In at least one example embodiment, the ratio of the volume of the imaging volume to the free volume partially encompassed by the field generation unit ranges between 0.1 and 0.5.

In at least one example embodiment, the ratio of the volume of the imaging volume to the free volume partially encompassed by the field generation unit ranges between 0.05 and 0.3.

In at least one example embodiment, a distance between an outer boundary of the imaging volume and a surface of the at least one magnet essentially coincides with a diameter of a sphere with the same volume as the imaging volume.

In at least one example embodiment, a minimum diameter of a sphere with a same volume as the imaging volume is in the range of 2 cm to 10 cm.

In at least one example embodiment, a maximum diameter of a sphere with the same volume as the imaging volume is in the range of 10 cm to 25 cm.

In at least one example embodiment, the at least one magnet comprises a permanent magnet or an array of permanent magnets.

In at least one example embodiment, the at least one magnet comprises a coiled wire.

In at least one example embodiment, the at least one magnet comprises high temperature superconducting materials and/or low temperature superconducting materials.

In at least one example embodiment, the at least one magnet comprises a combination of a permanent magnet, an array of permanent magnets, a coiled wire, a high temperature superconducting material and/or a low temperature superconducting material.

In at least one example embodiment, the supporting structure is movably mounted and/or comprises a positioning unit configured to adjust a position of the field generating unit with respect to an imaging object and/or facilitate the access to the imaging volume.

In at least one example embodiment, the supporting structure comprises a yoke and/or a flexible element that can be placed in different positions of the supporting structure to modify a position and/or a shape of the imaging volume to match the imaging object.

In at least one example embodiment, a shape of the supporting structure is designed to match a contour and/or a surface of the imaging object to enhance coverage of the imaging object.

In at least one example embodiment, the gradient field system is carried by the supporting structure.

In at least one example embodiment, the gradient field system comprises two gradient coils generating magnetic field gradients in a first direction and in a second direction oriented perpendicular to the first direction and wherein a spatial encoding in a third direction oriented perpendicular to the first direction and the second direction is accomplished via a static field gradient implemented by the B0 magnetic field.

In at least one example embodiment, the radiofrequency system is designed to match the contour and/or the surface of the imaging object to enhance coverage of the imaging object and/or decrease a distance between the at least one radiofrequency antenna and the surface of the imaging object.

In at least one example embodiment, the radiofrequency system is carried by the supporting structure and/or the field generation unit.

In at least one example embodiment, the radiofrequency system is configured to allow for an adjustment of a relative position of the radiofrequency system and/or a part of the radiofrequency system with respect to the imaging object.

In at least one example embodiment, the radiofrequency system comprises a support element for resting an imaging object and/or prevent movement of the imaging object.

In at least one example embodiment, the field generation unit comprises at least one symmetry plane and the direction of access to the imaging volume is oriented perpendicular to the main direction of magnetic field lines of the B0 magnetic field and parallel to the at least one symmetry plane of the field generation unit.

In at least one example embodiment, the field generation unit comprises at least two magnet sections, wherein the magnet sections are asymmetrically distributed over the field generation unit to adjust the position and/or the shape of the imaging volume to a shape of the imaging object and/or to facilitate access for the imaging object to the imaging volume.

In at least one example embodiment, the field generation unit comprises two symmetry planes.

In at least one example embodiment, a shape of the field generation unit is homeomorphic to a half-torus which is cut along a poloidal plane, wherein the opening is provided by the cut along the poloidal plane of the half-torus.

In at least one example embodiment, the field generation unit is designed to match at least a part of the contour and/or the surface of the imaging object to provide enhanced coverage of the imaging object.

In at least one example embodiment, a cross-section of the field generation unit and/or the supporting structure comprise one of a 'U' or a 'C' shape.

In at least one example embodiment, a cross-section of the field generation unit and/or the supporting structure comprise a 'Bell' shape.

In at least one example embodiment, a shape of the opening and/or the shape of the field generation unit are designed to compensate for a variance of a size, an orientation and/or the shape the imaging object.

In at least one example embodiment, the field generation unit comprises at least two magnet sections, which are arranged at an angle towards each other, forming an essentially triangular half-open space enclosing at least a part of the imaging volume, wherein the opening is provided by the half-open space between the at least two magnet sections.

In at least one example embodiment, the half-open space between the at least two magnet sections of the field generation unit provides access to the imaging volume in two essentially perpendicular directions.

In at least one example embodiment, a magnet section of the at least two magnet sections comprises one of a polygonal, a rectangular, an oval, an elliptic or a sickle-shaped cross-section, wherein the cross-section may be continuous or discontinuous.

In at least one example embodiment, the supporting structure comprises two ending plates carrying the at least two magnet sections, wherein the ending plates are arranged in accordance with the essentially triangular half-open space comprising the imaging volume.

In at least one example embodiment, the angle at which the at least two magnet sections are arranged comprises a value of more than 0 degrees and less than 180 degrees.

In at least one example embodiment, the angle at which the at least two magnet sections are arranged comprises a value between 60 degrees and 120 degrees.

In at least one example embodiment, the angle at which the at least two magnet sections are arranged comprises a value between 45 degrees and 115 degrees.

In at least one example embodiment, the angle at which the at least two magnet sections are arranged comprises a value between 10 degrees and 60 degrees to each other.

In at least one example embodiment, the gradient field system is carried by the ending plates of the supporting structure.

In at least one example embodiment, the at least one gradient coil of the gradient field system is positioned adjacent to at least one of the at least two magnet sections of the field generation unit.

In at least one example embodiment, the at least one gradient coil of the gradient field system is at least partially recessed into at least one of the at least two magnet sections.

In at least one example embodiment, the supporting structure comprises at least one movable joint to modify the angle and/or a relative position between the at least two magnetic sections.

In at least one example embodiment, the radiofrequency system comprises at least two radiofrequency antennas, wherein at least one radiofrequency antenna is carried by either one of the ending plates.

In at least one example embodiment, at least one radiofrequency antenna comprises a 90° phase shift of radiofrequency currents with respect to another radiofrequency antenna.

In at least one example embodiment, a radiofrequency antenna comprises a coil of wire.

In at least one example embodiment, the coil of wire comprises a lemniscate shape.

In at least one example embodiment, the coil of wire comprises an oval shape, a polygonal shape, a shape comprising a plurality of polygons and/or ovals or a shape obtained by twisting and/or distorting a polygon or an oval.

In at least one example embodiment, a radiofrequency antenna comprises a rod.

In at least one example embodiment, the radiofrequency system comprises a third antenna, which is positioned in a corner of the essentially triangular half-open space between the ending plates of the supporting structure.

In at least one example embodiment, the third antenna comprises a 90° phase shift of radiofrequency currents with respect to at least one other radiofrequency antenna of the radiofrequency system.

In at least one example embodiment, an amplitude of each radiofrequency antenna for transmitting of radiofrequency radiation is weighted by a splitter network to generate a homogenous and circularly polarized B1 magnetic field and/or a linearly polarized B1 magnetic field.

In at least one example embodiment, the imaging volume comprises a plurality of sub-regions with different levels of magnetic field variability, whereby different imaging methods are applied, depending on the level of magnetic field variability in a sub-region.

In at least one example embodiment, the imaging volume comprises a first sub-region with a maximum tolerable field variability and a second sub-region with a higher tolerable field variability than the maximum tolerable field variability of the first sub-region.

In at least one example embodiment, the imaging volume comprises at least a third sub-region with a higher tolerable field variability than the maximum tolerable field variability of the second sub-region.

In at least one example embodiment, the supporting structure and/or the field generation unit comprise at least one hole or recess to provide an unobstructed view through the magnetic resonance imaging system and/or enhance airflow to the imaging volume and/or provide access for intervention or therapy measures.

In at least one example embodiment, a shape of the imaging volume is characterized by a predefined variability of the B0 magnetic field and the variability of the B0 magnetic field is disposed in a way, that the shape of the imaging volume is essentially non-spherical.

In at least one example embodiment, the shape of the imaging volume is ellipsoidal, conical, toroidal or cuboid.

In at least one example embodiment, a cross-section of the imaging volume comprises an oval shape or a polygonal shape.

FIG. 1 depicts a schematic representation of a magnetic resonance imaging system 10 configured to perform a magnetic resonance imaging examination of a jaw region and/or an eye region of a patient 15 according to at least one example embodiment. An application of the magnetic resonance imaging system 10 for imaging of the jaw region and/or the eye region of the patient 15 is to be understood as an example. The magnetic resonance imaging system 10 may also be configured to perform cardiac imaging of a heart: e. g. enabling physical exercise during an imaging examination and better physiological monitoring due to improved openness, as well as enhanced possibilities for interventions, such as catheter procedure and access for intra-venous stress or contrast agents, mammography imaging of a breast: covering of either a single breast or both breasts in one imaging volume 30 or provision of two symmetric individual imaging volumes 30, neurological imaging of a brain and/or a spine: enhancing treatment and/or stimulation during an imaging examination, combination with other sensors like EEG, avoiding contra-indications associated with deep brain stimulators, orthopedics imaging of joints (e.g. knee, shoulder, elbow): enabling movement of the joints to allow dynamic and/or functional imaging, ophthalmologic imaging of an eye, two eyes, an optic nerve and related anatomy: either covering both eyes in one imaging volume 30 or allowing a subsequent scanning of either side in a dedicated imaging volume 30, as well as covering orbits and optic nerves in separate imaging examinations (or imaging sequences); enabling combination of magnetic resonance imaging with other diagnostic modalities like optical coherence tomography, ultrasound, optical cameras and the like, dental imaging of a jaw and/or teeth: advantageous positioning and orientation of the magnets 14 in the field generation unit 12 (e. g. 45-degree angulation of the yoke as shown below) to provide enhanced coverage of the jaws, possibly supported via a dedicated intra-oral radiofrequency antenna 32, imaging the prostate: orienting the access to the half-open space 47 in such a way that the patient 15 can sit on the field generation unit 12 and/or the magnetic resonance imaging system 10 to provide best possible access to the prostate region (e. g. with the magnet opening oriented upward), imaging of the ear, nose and throat region with a dedicated radiofrequency antenna 32 or imaging of other body regions of the patient 15. For these imaging applications, the field generation unit 12 of the magnetic resonance imaging system 10 may be positioned and/or oriented relative to a diagnostically relevant body region (target anatomy) of the patient 15 via the positioning unit 29.

Furthermore, the magnetic resonance imaging system 10 may be used in veterinary care to visualize body regions of animals, for example extremities of large animals like horses or cows. The opening 48 to the imaging volume 30 may be oriented upward to provide an easy access for placing the animal (e. g. cat, dog, hamster, etc.) on appropriate positioning aids and cushions.

The magnetic resonance imaging system 10 depicted in FIG. 1 comprises a field generation unit 12 with a first magnet 14a and a second magnet 14b. In the present example, the first magnet 14a and the second magnet 14b are carried by a supporting structure 11 which maintains a predefined distance between the first magnet 14a and the second magnet 14b. The supporting structure 11 may also be implemented as an iron yoke 18. A free volume between the first magnet 14a and the second magnet 14b represents an image acquisition region 17 configured to receive an examination object 15, e. g. a body region of the patient 15. The image acquisition region 17 is confined by the field generation unit 12 in two spatial directions. The image acquisition region 17 may correspond to a half-open space 47 between the first magnet 14a and the second magnet 14b. The patient 15 may be positioned within the image acquisition region 17 by a patient positioning device 16. However, the magnetic resonance imaging system 10 may also comprise a positioning unit 13 for adjusting a position and/or an orientation of the field generation unit 12 with respect to the patient 15. For example, the positioning unit 13 may comprise a swivel joint configured to rotate the field generation unit 12 along a rotation direction WX and/or a rotation direction WY. A position of the field generation unit 12 along a Y-direction and/or a Z-direction may be adjusted via a suitable telescope system and/or rail system mechanically connected to the supporting structure 11. Of course, other embodiments of the supporting structure 11 and/or the positioning unit 13 are possible. In particular, the positioning unit 13 may further be configured to position the field generation unit 12 along an X direction and/or rotate the field generation unit 12 in a WZ direction.

The first magnet 14a and the second magnet 14b are configured to generate a magnetic field in the image acquisition region 17. The field generation unit 12 may further comprise a gradient field system 27 (not shown in FIG. 1) with at least one gradient coil 28 for generating magnetic gradient fields used for spatial encoding of magnetic resonance signals acquired during a magnetic resonance imaging examination. Preferably, the field generation unit 12 comprises a radiofrequency system 29 (not shown in FIG. 1) with at least one radiofrequency antenna 32 configured to emit a radiofrequency excitation pulse (radiofrequency radiation) in the image acquisition region 17. The at least one radiofrequency antenna 32 may also be configured to receive magnetic resonance signals from the image acquisition region 17, in particular the imaging volume 30. The at least one radiofrequency antenna 32 may also be configured as a local coil.

In order to control the field generation unit 12 as well as the at least one radiofrequency antenna 32, the magnetic resonance imaging system 10 comprises a control unit 20. The control unit 20 is configured to control the magnetic resonance imaging system 10 to perform an imaging examination. For this purpose, the control unit 20 may comprise a signal connection with a gradient control unit 21 and a radiofrequency antenna control unit 22. In at least one example embodiment, the gradient control unit 21 and the radiofrequency antenna control unit 22 are integrated within the control unit 20. Furthermore, the control unit 20 may comprise a processing unit 24 configured to coordinate an acquisition of magnetic resonance image data and/or a reconstruction of magnetic resonance image data acquired from the imaging volume 30. In at least one example embodiment, the processing unit 24 is also configured to evaluate and process data, such as magnetic resonance signals and/or magnetic resonance image data. The control unit 20 may comprise a controller, a microcontroller, an analog circuit, a logic unit and the like. The processing unit 24 may comprise a processor, such as a CPU, a GPU and the like. In at least one example embodiment, the control unit 20 and/or the processing unit 24 comprise a memory and/or an internal storage, such as a RAM, a ROM, a PROM, an EPROM, an EEPROM, a flash memory, as well as an HDD, an SSD and the like. The processing unit 24 may be configured to perform functions and algorithms described herein by executing computer readable instructions stored in a memory and/or an internal storage.

Control information, such as imaging parameters and/or magnetic resonance image data, can be displayed on an output unit 25. The output unit 25 may comprise at least one monitor configured to display control information and/or images acquired via the magnetic resonance imaging system 10 to an operator of the magnetic resonance imaging system 10. The magnetic resonance imaging system 10 may further comprise an input unit 26 configured to receive information and/or parameters input by the operator during an imaging examination.

The illustrated magnetic resonance imaging system 10 may of course include further components that magnetic resonance imaging systems usually comprise. The general mode of operation of a magnetic resonance imaging system 10 is well-known to the skilled person. Thus, a further description of the general components or a sequencing of an imaging examination is not deemed necessary. Furthermore, the magnetic resonance imaging system 10 may comprise different arrangements of the field generation unit 12. Possible system configurations may involve a triangular shape, a 'U' shape (or 'C' shape), a 'Bell' shape and similar configurations according to an embodiment described below.

In an example embodiment, the magnetic resonance imaging system 10 may be a dedicated scanner for dental imaging applications. For this purpose, anatomy-specific adaptions of the field generation unit 12 and/or the supporting structure 11 may enhance enclosure of a jaw region of the patient 15 with magnetic material and/or radiofrequency antennas 32. In at least one example embodiment, radiofrequency antennas 32 are provided intraorally, e. g. as local coils positioned in the mouth of the patient 15. Furthermore, the field generation unit 12 and/or the supporting structure 11 may be configured to provide a clearance for a nose of the patient 15 (see FIGS. 4a-4c) in order to enhance coverage of the target anatomy with magnetic material and/or to improve positioning of the target anatomy relative to the imaging volume 30.

Figure 2:
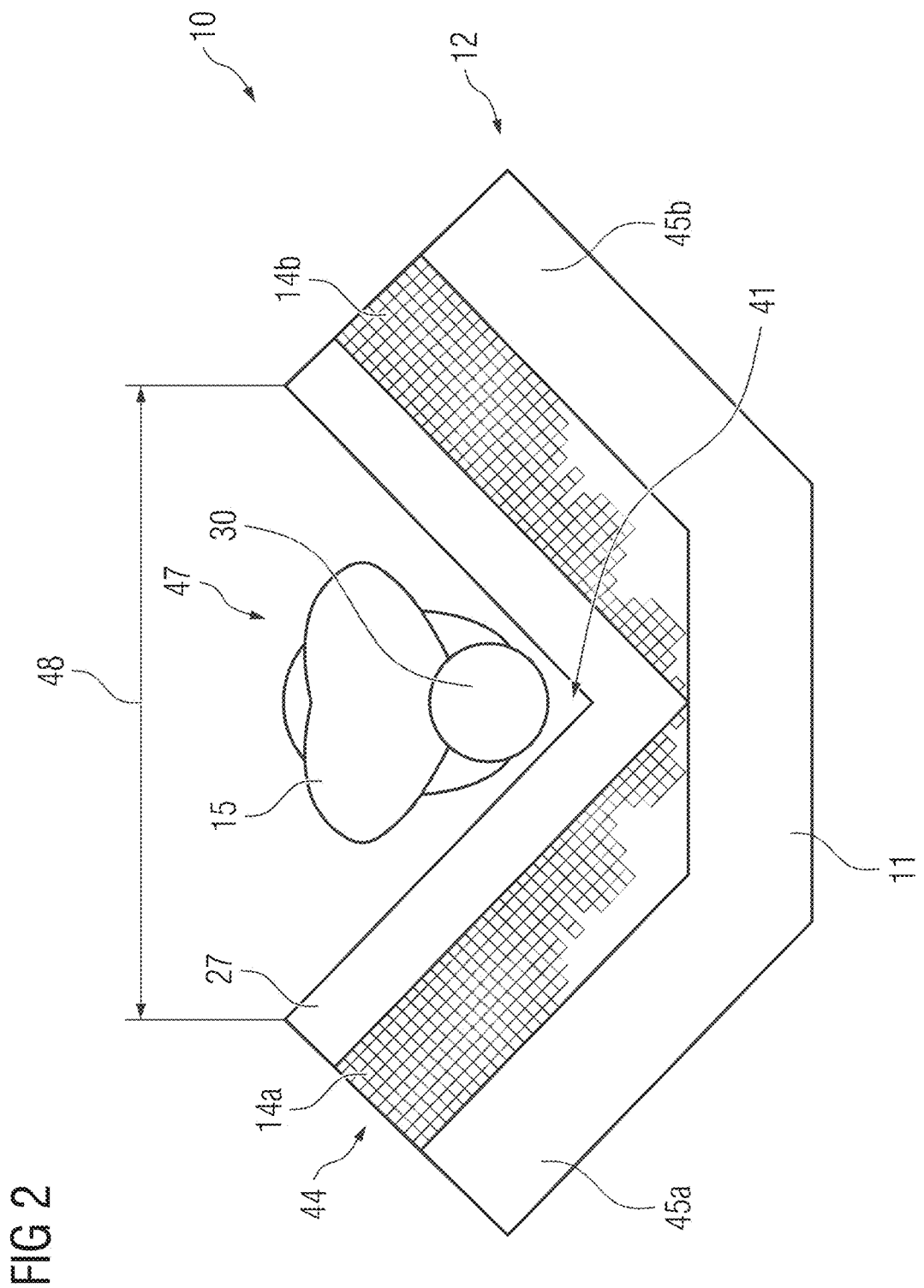
FIG. 2 illustrates a representation of an embodiment of a magnetic resonance imaging system.
Figure 13:
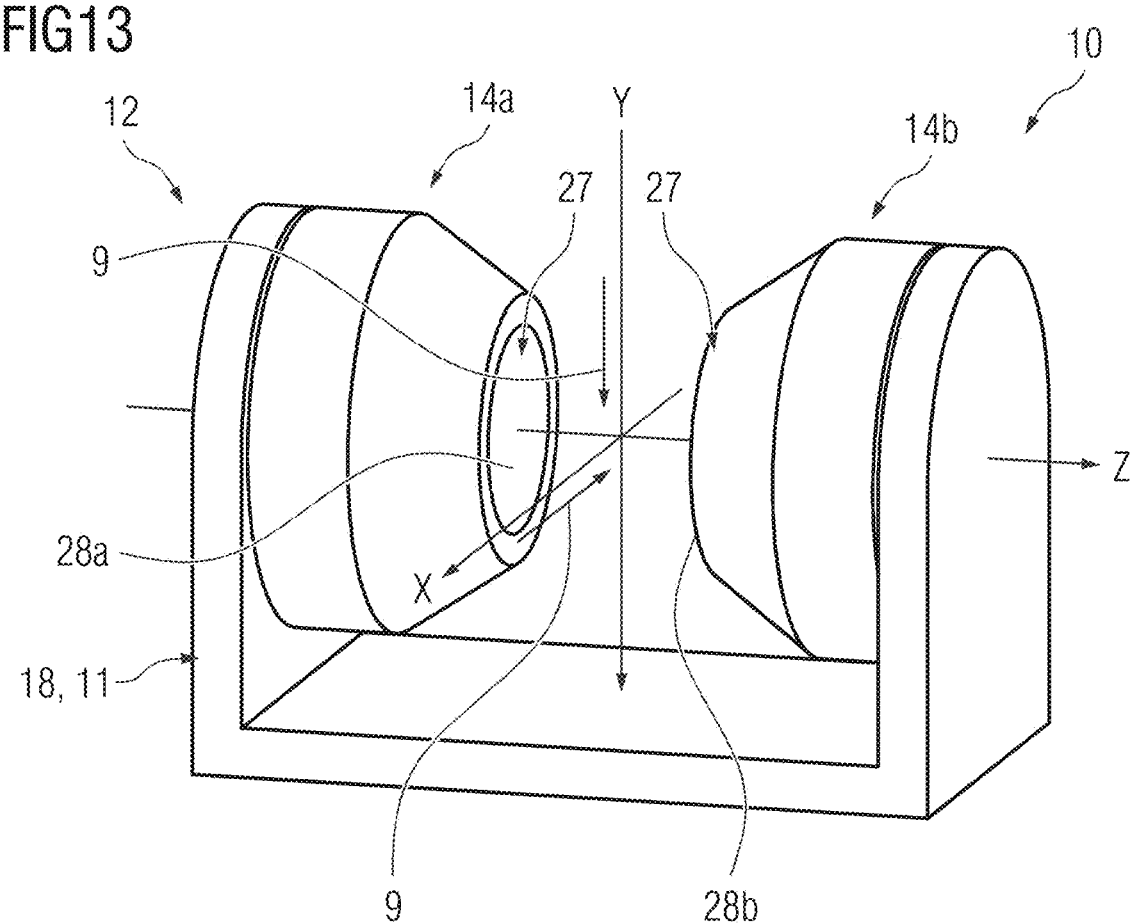
FIG. 13 illustrates a representation of an embodiment of an magnetic resonance imaging system.

FIG. 2 shows an embodiment, wherein the field generation unit 12 comprises a triangular shape. It shall be understood that the features and embodiments described in connection with the triangular shape may also be applicable to a 'U'-shaped (see e.g. FIG. 9,), a 'C'-shaped (see e.g. FIG. 13) or a 'Bell'-shaped (see e.g. FIGS. 21a-21c) magnetic resonance imaging system 10 and vice versa, unless stated otherwise.

A triangular magnetic resonance imaging system 10 may comprise a supporting structure 11 comprising two ending plates 45a and 45b, which are arranged at an angle of more than 0 degrees and less than 180 degrees. In at least one example embodiment, the angle between the ending plates 45a and 45b is in the range of 30-150 degrees, 0-20 degrees, 20-40 degrees, 40-60 degrees, 60-80 degrees, 80-100 degrees, 100-120 degrees and so forth. The field generation unit 12 may comprise at least two magnet sections 14a and 14b, which are arranged in a triangular configuration, comprising an angle of more than 0 degrees and less than 180 degrees, thus providing a 'half-open' space 47 enclosing at least a part of the imaging volume 30.

In one embodiment, the magnet sections 14a and 14b are carried by the ending plates 45a and 45b of the supporting structure 11. A width of an opening 48 of the triangular magnetic resonance imaging system 10 may range between 10 and 30 cm, 20 and 40 cm, 40 and 80 cm or 60 and 100 cm, thus providing enough clearance to ensure an easy access of an imaging object to the imaging volume 30. In the embodiment depicted in FIG. 2, the width of the opening 48 is about 60 cm. The cross-sections 44 of the magnet sections 14a and 14b and the supporting structure 11 may both comprise a thickness of about 10 cm and the gradient field system 27 may comprise a thickness of 5 cm. The given dimensions are to be viewed as example values and may differ depending on a specific implementation of technical features of the proposed magnetic resonance imaging system 10. In at least one example embodiment, the magnetic resonance imaging system 10 comprises a patient cover or cushion between the gradient field system 27 and the patient 15, in order to protect the patient 15 from electric currents and/or enhance comfort during an imaging examination.

In one embodiment, an angle between the magnet sections 14a and 14b is essentially 90 degrees. The half-open space 47 between the magnet sections 14a and 14b may comprise a corner 41 or nook where the ending plates 45a and 45b are attached and/or connected. In at least one example embodiment, the half-open space 47 comprises a homogeneous magnetic field in proximity to the corner 41 or nook. However, the triangular magnetic resonance imaging system 10 does not have to comprise orthogonally oriented magnet sections 14a and 14b. In the cross-sectional view provided in FIG. 2, the magnetic resonance imaging system 10 may also resemble an 'L', a 'V' or include rounded sections, as found for example in a 'U'.

In one embodiment, the magnetic resonance imaging system 10 comprises an open magnet with non-parallel but flat pole faces. The pole faces may at least partially be covered by coils of a gradient field system 27 and/or a radiofrequency system 29.

The field generation unit 12 may comprise permanent magnets (e. g. ferromagnets), pole elements (e.g. induced magnets such as iron or other ferromagnetic materials) and/or coils (such as resistive coils or low- or high temperature superconductors). It may further comprise an array of magnets 14 (including a bulk superconductor) of uniform or variable magnetic strength and orientation. An array of magnets 14 may also be implemented as an array of coils with either flat coils or coils having a defined curvature in a winding plane.

FIG. 3 shows a schematic representation of a triangular magnetic resonance imaging system 10, wherein the field generation unit 12 comprises two symmetry planes 46a and 46b. The dashed lines represent the intersections with the symmetry planes of the triangular magnetic resonance imaging system 10.

Figure 11A:
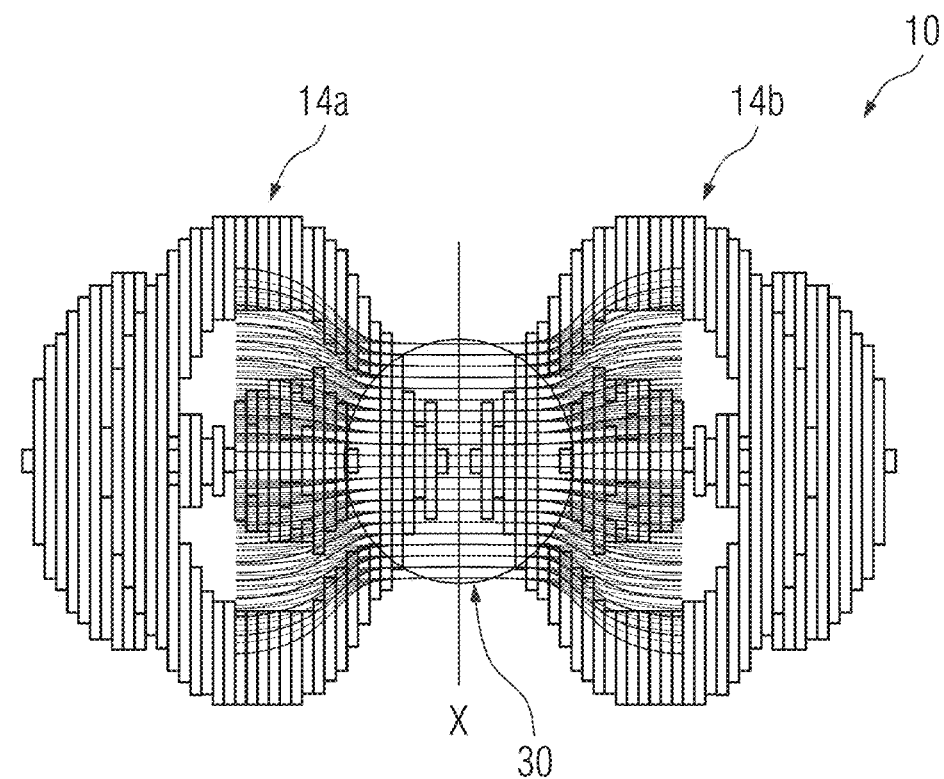
FIGS. 11a-11b illustrate a representation of a magnetic field provided by an embodiment of a magnetic resonance imaging system.
Figure 11B:
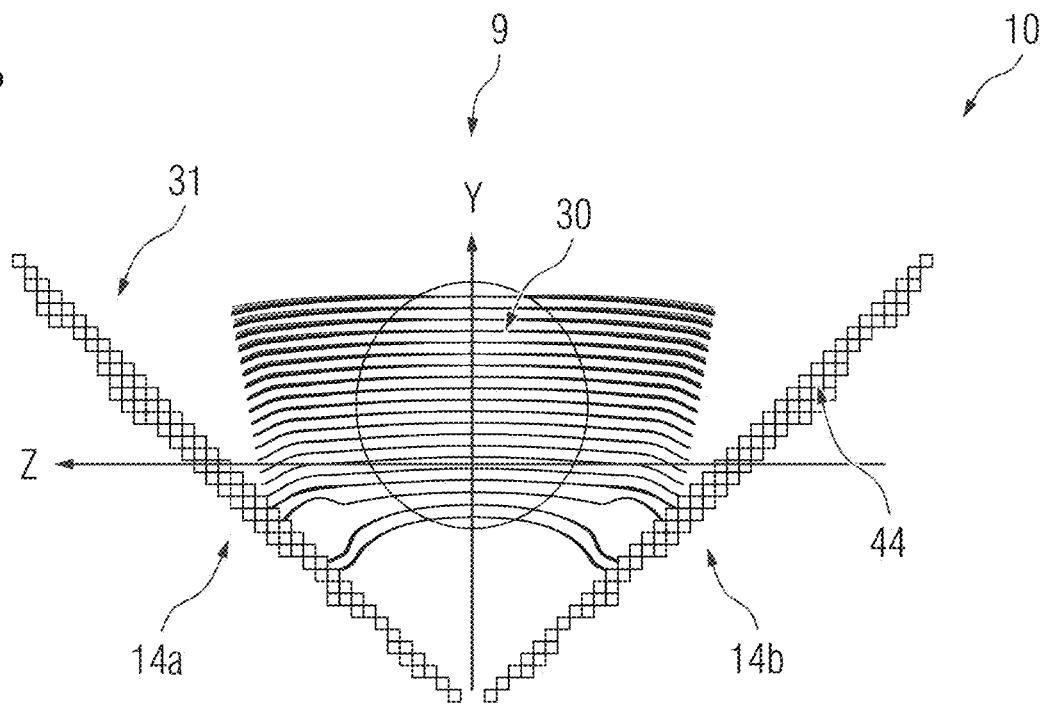

A direction of access 9 to the imaging volume 30 is oriented perpendicular to a B0 magnetic field direction and parallel to a symmetry plane of the field generation unit (see FIG. 11b). The field generation unit 12 may further provide access to the imaging volume 30 in two essentially orthogonal directions: one direction of access along the Y-direction and one direction of access along the X-direction (see FIGS. 11a-11b).

In one embodiment, the magnet sections 14a and 14b are asymmetrically distributed over the field generation unit 12. However, the magnetic resonance imaging system 10 may still comprise one symmetry plane along a line of the corner 41 of the half-open space 47.

In an embodiment, the supporting structure 11 of the magnetic resonance imaging system 10 comprises a yoke 18 attached to at least one magnet 14 in order to increase and/or improve magnetic flux density. The yoke 18 may be designed to optimize field enforcing and shaping while keeping enough free space to allow for positioning of an imaging object in the half-open space 47. In at least one example embodiment, the yoke 18 is positioned on a backside of the magnetic resonance imaging system 10, thus ensuring best possible access to the imaging volume 30. However, the yoke 18 may also be installed at the top of the magnetic resonance imaging system 10. Thus, the yoke may confine the imaging volume 30 in at least one spatial direction.

In a further embodiment, the supporting structure 11 or parts of the supporting structure 11 are movable and can be opened and/or tilted to provide easier access to the imaging volume 30. In at least one example embodiment, the supporting structure 11 and/or the yoke 18 comprise at least one flexible element (not shown) to modify a position, a shape and/or an arrangement of the supporting structure 11 and/or the imaging volume 30. A flexible element may be a separate piece of the yoke 18 or the supporting structure 11, that may be placed in a predefined position to adjust the magnetic flux density. In at least one example embodiment, the supporting structure 11 (and/or a positioning unit 13) comprises a hinge or other form of movable joint in order to modify the angle and/or the relative position between the ending plates 45a, 45b and/or the magnet sections 14a, 14b of the field generation unit 12. Such a change may facilitate accessing the half-open space 47 and/or modify the magnetic field to match the imaging volume 30 to a specific imaging object.

Figure 4C:
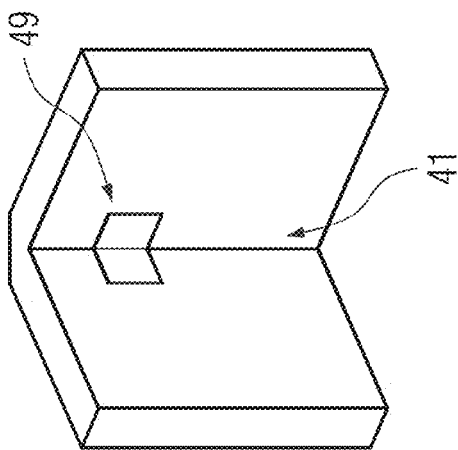
FIGS. 4a-4c illustrates a schematic representation of embodiments of a magnetic resonance imaging system.
Figure 4B:
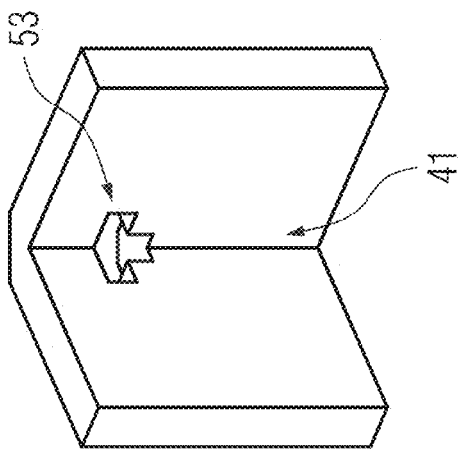
Figure 4A:
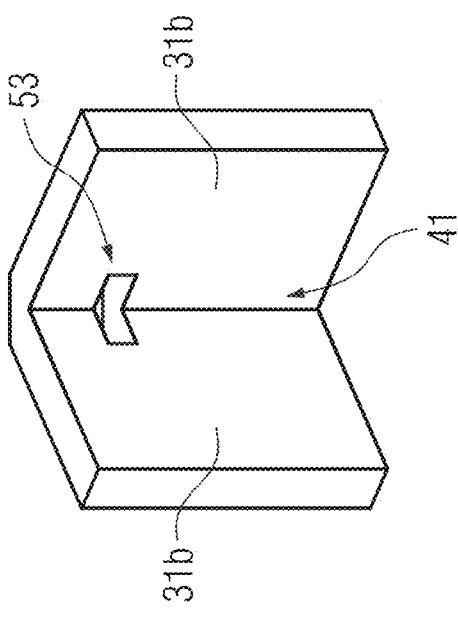

FIGS. 4a-4c holds a schematic representation of embodiments of the magnetic resonance imaging system 10 which increase patient comfort by providing a hole 53 or a display 49 positioned at the corner 41. In one embodiment depicted in FIGS. 4a-4b, the supporting structure 11 and/or the field generation unit 12 comprise at least one hole 53 or recess in order to provide an unobstructed view through the magnetic resonance imaging system 10 and/or enhance airflow to the imaging volume 30. In at least one example embodiment, further holes or cavities are distributed along the corner 41 and/or the pole faces 31a and 31b of the magnetic resonance imaging system 10 to improve an access to the patient 15 positioned in the half-open space 47 during interventions and/or therapy. As shown in FIG. 4b, the at least one hole 53 may also be enlarged to accommodate a nose of the patient 15 and/or improve air flow to the imaging volume 30 and/or the patient 15. The at least one hole 53 or recess may be positioned in the magnet 14a, 14b and/or in the ending plate 45a, 45b of the supporting structure 11. Wires of the gradient field system, the radiofrequency system 29 and/or magnets 14a, 14b may be routed around the at least one hole 53 or recess.

In one embodiment depicted in FIG. 4c, a display 49 is installed on in the corner 41 of the half-open space 47 in order to output visual information to the patient 15. A surface of the display 49 may be flush with an interior surface of the half-open space 47 or the display 49 may be recessed within the supporting structure 11 and/or the magnet sections 14a and 14b of field generation unit 12. In at least one example embodiment, the display 49 is positioned behind the magnetic resonance imaging system 10 and the patient 15 may see the display 49 through dedicated cut-outs in the supporting structure 11 and/or the field generation unit 12. The display 49 may provide arbitrary visual information. For example, the display 49 may provide a video stream from a camera 54 positioned in an imaging room (see e.g. FIG. 8), as well as medical or educational information and/or entertaining content.

In one embodiment, the magnetic resonance imaging system 10 comprises an auditory system (not shown) to allow for a communication with the patient 15 and/or an instruction of the patient 15. In at least one example embodiment, the auditory system provides entertaining or educational information to the patient 15 during an imaging examination. The auditory system may comprise a speaker, a headphone, an ear plug, or any other device that allows to provide sound and/or auditory information to the patient 15. In one embodiment, the auditory system is carried by the supporting structure 11 and/or the field generation unit 12 of the magnetic resonance imaging system 10.

Figure 6:
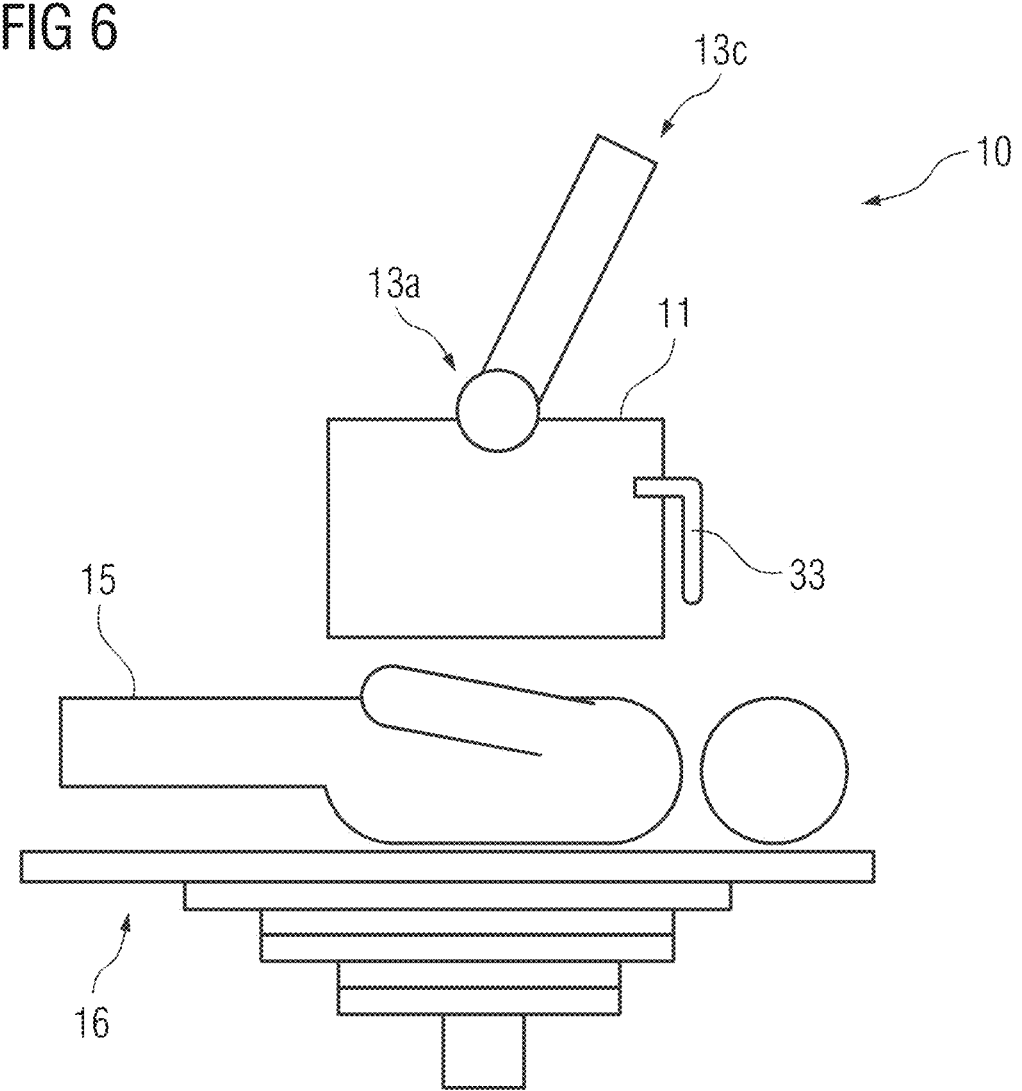
FIG. 6 illustrates a schematic representation of an embodiment of a magnetic resonance imaging system.
Figure 7:
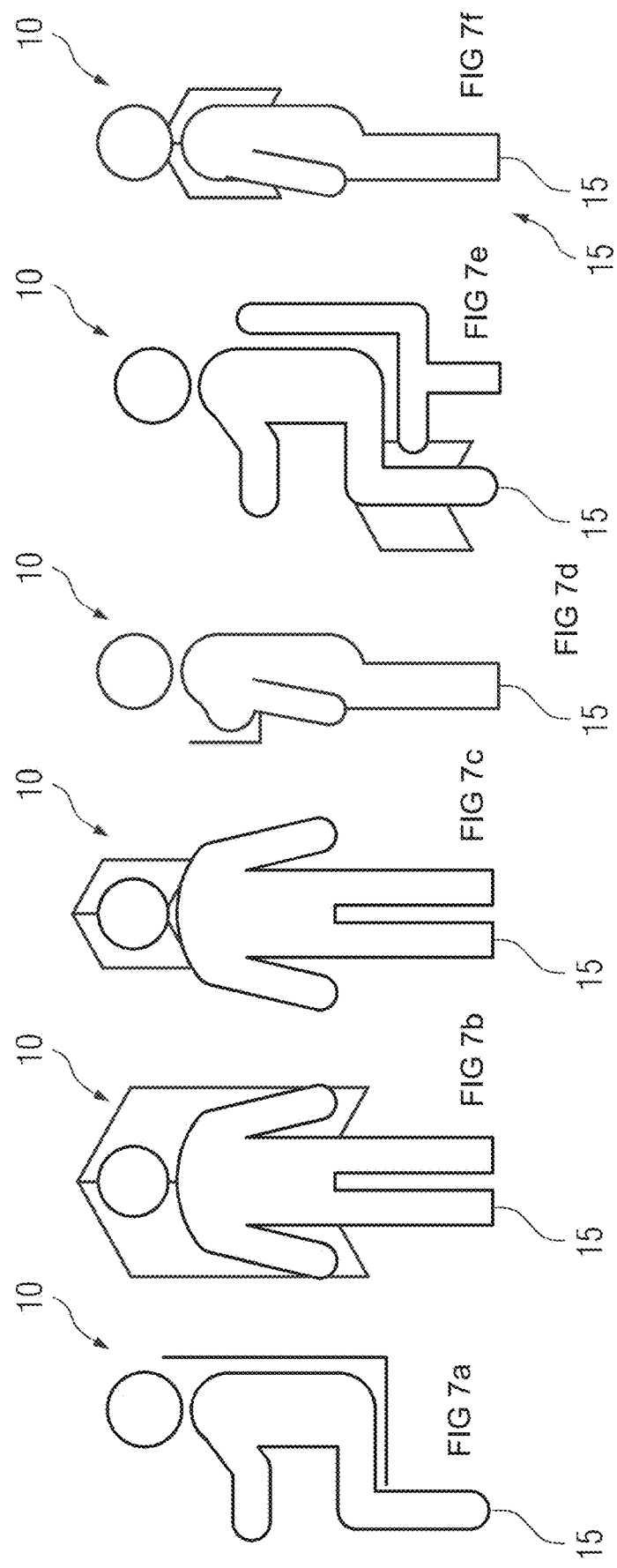
FIGS. 7a-7f illustrates a schematic representation of possible positions of a patient in a magnetic resonance imaging system.

FIGS. 5 and 6 show different embodiments of a positioning unit 13 of the magnetic resonance imaging system 10. According to the embodiment presented in FIG. 5, the supporting structure 11 of the magnetic resonance imaging system 10 is attached to a positioning unit 13a, such as a post or a wall mount. The supporting structure 11 and/or the positioning unit 13a may comprise at least one movable joint and/or hinge to allow for a 3D movement of the field generation unit 12. For example, an orientation of the magnetic resonance imaging system 10 may be adjusted along the WY-direction and/or the WX-direction. A height of the magnetic resonance imaging system 10 may be adjusted along the Y-direction. Of course, it is also possible to adjust the position and/or orientation of the magnetic resonance imaging system 10 along further spatial directions via the positioning unit 13. The field generation unit 12 may be moved manually with a handle 33, e. g. by the medical staff, or automatically, e.g. via electric, pneumatic and/or hydraulic drives. In at least one example embodiment, the magnetic resonance imaging system 10 is adjusted via a remote-control system, either operated by members of the medical staff or operated autonomously with the aid of dedicated sensors and/or cameras 54. In FIG. 5, imaging of the patient 15 may be performed in an upright or standing position of the patient 15. However, it is also possible to provide a patient positioning device 16 allowing the patient 15 to be imaged in an essentially horizontal position. As depicted in FIG. 6, the positioning unit 13 may further comprise a moveable hinge or joint 13a and an arm 13c, which may be attached to the supporting structure 11 in order to extend a moving range of the magnetic resonance imaging system 10. As described above, an orientation and/or a position of the magnetic resonance imaging system 10 may be adjusted via the positioning unit 13 along a plurality of spatial directions.

In one embodiment, a half-open space 47 between two magnets 14a and 14b of the magnetic resonance imaging system 10 may be used as a basis for a plurality of dedicated imaging postures as shown in FIGS. 7a-7f. For example, the corner 41 of the triangular, half-open space 47 may be oriented vertically in order to examine the spine of the patient 15 in an upright or standing position as depicted in FIGS. 7b-7d and 7f). A magnetic resonance imaging system 10 of smaller dimensions could also accommodate the head and/or the jaw region (see FIG. 7c), as well as shoulders and/or extremities (see FIGS. 7e and 7f) of the patient 15. A chair like configuration appears particularly attractive for imaging the lower abdomen and/or the prostate (see FIG. 7a), whereas a shelf like configuration appears attractive for a breast imaging examination (see FIG. 7d).

A mounting of the magnetic resonance imaging system 10 may be different depending on a target anatomy. Regarding FIG. 7a, a floor mounted magnetic resonance imaging system 10 may be provided. However, in at least one example embodiment, the magnetic resonance imaging system 10 is movably mounted via a positioning unit 13 (see e.g. FIGS. 1, 5 and 6) and allows for a plurality of different positions and/or postures of the patient 15 as shown in FIGS. 7a-7f.

In one embodiment of the magnetic resonance imaging system 10, the patient 15 can be moved relative to the field generation unit 12 via the patient positioning device 16 to progressively cover a target anatomy. The succession of coverage may be left-to-right, (e. g. covering one hemisphere in one go) or upper-to-lower part of an anatomy (e. g. in standing position), as well as front-to-back. Alternatively, the field generation unit 12 may be moved relative to the patient 15 via the positioning unit 13.

The movement of the patient 15 or the field generation unit 12 may be accomplished either by manual guidance, e.g. supported by mechanical rails of the positioning unit 13a (see FIG. 5) defining an extent of an overall spatial coverage, or by electric, hydraulic and/or pneumatic drives. In at least one example embodiment, the movement is controlled by the control unit 20 and/or the processing unit 24. The control unit 20 and/or the processing unit 24 may acquire and/or take into account initial information, such as signals from an optical camera 54, patient specific parameters like age, size, weight or disease specific coverage demands. The current relative position and/or orientation of the magnetic resonance imaging system 10 and the imaging object may also be tracked, based on information from a camera 54, an optical measurement device (e. g. LASER, infrared light), an ultrasound distance measurement device and the like. This information may be fed into the processing unit 24 for reconstruction and proper spatial alignment of the measured data.

In one embodiment, the proposed magnetic resonance imaging system 10 may provide multi-slab imaging, wherein a volume larger than the imaging volume 30 is imaged. Multi-slab imaging may involve changing a relative position between the field generation unit 12 and the imaging object. In at least one example embodiment, a relative motion between the field generation unit 12 and the imaging object is continuous or discontinuous. I In at least one example embodiment, a plurality of images is acquired, from which a coherent image of the imaging object is reconstructed. The relative motion between the field generation unit 12 and the imaging object may be implemented via motion of the magnetic resonance imaging system 10 with respect to the imaging object and/or motion of the imaging object relative to the field generation unit 12. In the latter case, a patient positioning device 16 may be used to stabilize the patient 15 and ensure a predefined motion of the patient 15 through the half-open space 47 of the field generation unit 12.

Figure 8:
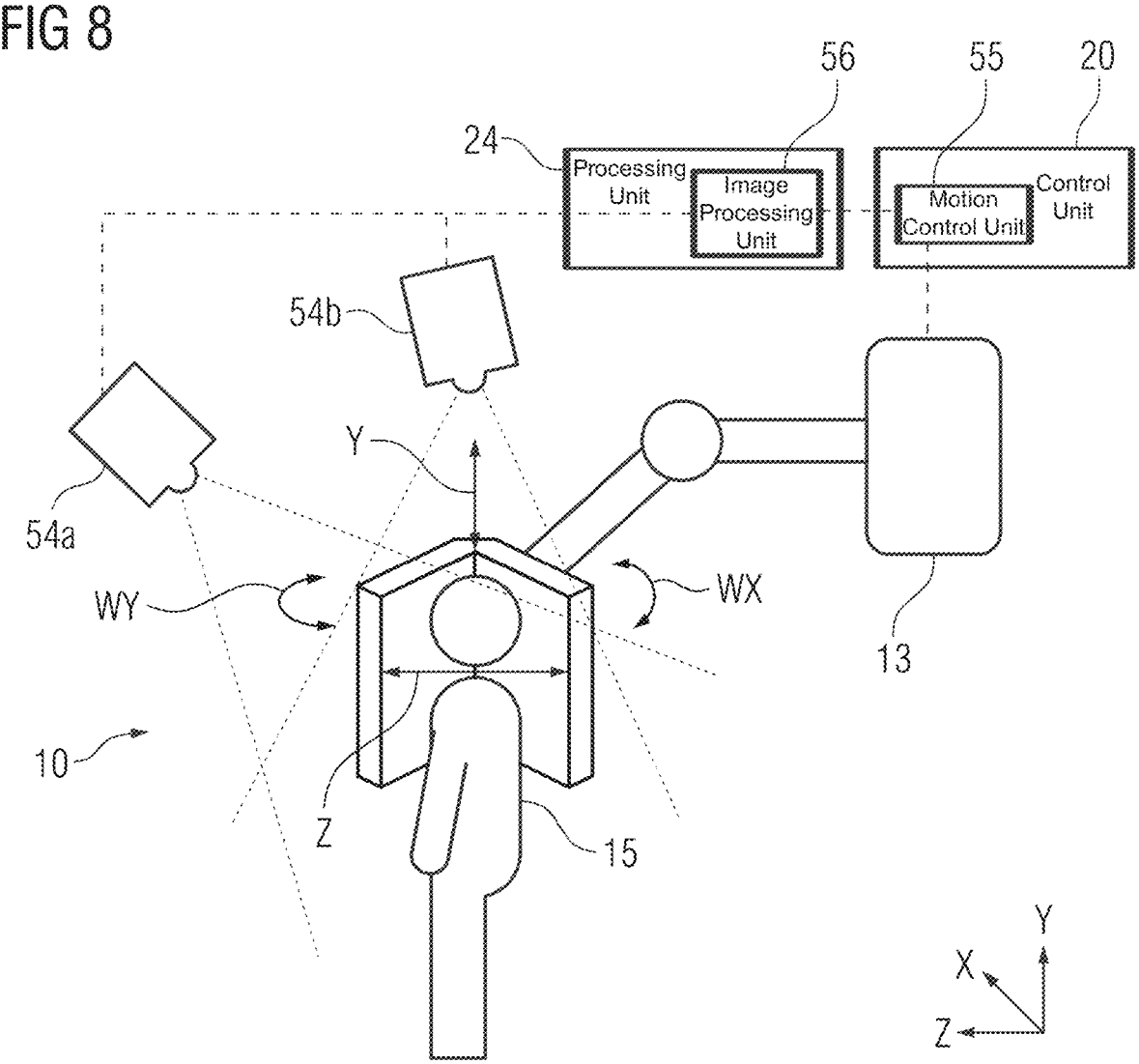
FIG. 8 illustrates a schematic representation of an embodiment of a magnetic resonance imaging system.

In an embodiment of the magnetic resonance imaging system 10 depicted in FIG. 8, a signal from a camera system comprising at least one camera 54 may be fed into an image processing unit 56 of the processing unit 24. The image processing unit 56 is configured to process the signal and determine the relative positions of the imaging object and the field generation unit 12 in dependence of the signal. The image processing unit 56 and/or the processing unit 24 may be configured to determine a position and/or orientation required for a present imaging examination and transmit necessary coordinates of the field generation unit 12 to a motion control unit 55 of the control unit 20. The motion control unit 55 may then implement instructions regarding the position and/or orientation required for the present imaging examination and translate the movement to the field generation unit 12 via dedicated motion actuators incorporated in the positioning unit 13. In at least one example embodiment, other sensors (e. g. an optical sensor or an ultrasound distance measurement device) are used independently or combined with information from a camera system. The image processing unit 56 (or signal processing unit) and/or the motion control unit 55 may be integrated within the processing unit 24 and the control unit 20 as described above or be integrated into the positioning unit 13 of the magnetic resonance imaging system 10. Furthermore, a wireless communication between the sensors and the magnetic resonance imaging system 10 may be included.

FIG. 9 depicts an embodiment of the magnetic resonance imaging system 10, wherein the field generation unit 12 comprises two magnets 14a and 14b, which are positioned on substantially opposing sides of the imaging volume 30. The field generation unit 12 may comprise two gradient coils 27a and 27b positioned adjacent to the magnets 14a and 14b. Furthermore, two radiofrequency antennas may be positioned adjacent to the gradient coils 27a and 27b and/or the magnets 14a and 14b. The field generation unit 12 of the magnetic resonance imaging system 10 depicted in FIG. 9 may comprise a U-shape, a C-shape or a shape of a half-torus cut along a poloidal plane.

In one embodiment, the field generation unit 12 may be configured to optimize the B0 magnetic field homogeneity in one or more selected volumes 30a and 30b of a plurality of volumes or sections of the imaging volume 30. In at least one example embodiment, the imaging volume 30 comprises several sub-regions with differing levels of magnetic field homogeneity. In a simple example, a first sub-region 30a may comprise a maximum tolerable magnetic field variability of 100 ppm. A second sub-region 30b, encompassing the first sub-region 30a, may comprise a maximum tolerable field variability of 1000 ppm. This concept may be extended to more regions, e. g. a third sub-region or a fourth sub-region. In at least one example embodiment, different sub-regions are positioned adjacent to each other or at least partially overlap.

Different imaging methods may be applied, which are compatible with different levels of magnetic field variability. For example, a useable imaging volume for a PETRA (pointwise encoding time reduction with radial acquisition) sequence may comprise the second sub-region 30b with a diameter of 15 cm, whereas for a conventional cartesian TSE (turbo spin echo) sequence, a useable imaging volume may comprise only the first sub-region 30a with a diameter of 10 cm. From an application development point of view, the distinction of sub-regions with differing levels of magnetic field homogeneity may put some constraint to an imaging examination workflow. As an example, a coverage of an anatomy may be compromised in favor of a contrast and/or an efficiency of the imaging examination. However, different levels of magnetic field variability provide a degree of freedom regarding a design of the magnetic resonance imaging system 10 and represent a new aspect of designing magnetic resonance imaging systems. Providing high field efficiencies in a reduced imaging volume represented by a field homogeneity not exceeding a certain threshold may be an appropriate solution for some imaging applications.

In one embodiment, the magnetic resonance imaging system 10 comprises a homogeneous volume (defined as suitable for near-'classic' imaging), completely or approximately contained within the half-open space 47 encompassed by the field generation unit 12. A homogeneous volume may comprise a deviation from a target magnetic field strength within the imaging volume 30 of less than 5000 ppm, 1000 ppm, 200 ppm, 100 ppm, 50 ppm, 20 ppm, 10 ppm, 5 ppm, 2 ppm or less than 1 ppm. The requirements of field homogeneity may be lowered in comparison to conventional clinical magnetic resonance imaging systems, by using imaging techniques which are less susceptible to off-resonance, as there are short echo time sequences like UTE (ultra-short echo time), ZTE (zero echo time), SWIFT (sweep imaging with Fourier transformation), and PETRA.

Another approach for lowering the requirements for highest field homogeneity is to combine the magnetic resonance imaging system 10 with imaging methods currently used to reduce artefacts due to susceptibility variations in the presence of metal implants, like SEMAC-VAT (slice encoding for metal artifact correction with view angle tilting gradient) and MSVAT-SPACE (multiple-slab acquisition with view angle tilting gradient, based on a sampling perfection with application-optimized contrasts using different flip angle evolution). These sequences trade scan efficiency versus field homogeneity tolerance, but still remain in the regime of conventional fast imaging methods, in contrast to other approaches, which assume a higher level of field inhomogeneity, but typically at the expense of an extended duration of an imaging examination by orders of magnitude.

FIG. 10 shows an embodiment of the magnetic resonance imaging system 10 comprising at least one symmetry plane 46 oriented in parallel to the X- and Y-direction. The symmetry plane 46 may contribute to enhancing the magnetic field homogeneity in the center of the imaging volume 30. The magnet 14 of the field generation unit 12 may comprise a plurality of magnet sections 14a and 14b, which may be solitary or connected along the corner 41 of the half-open space 47. In the embodiment shown in FIG. 10, the field generation unit 12 is composed of an array of permanent magnets with different sizes and orientations. The permanent magnets may be arranged along ending plates 45a and 45b of the supporting structure 11 (see FIG. 2) and the pole faces 31a and 31b of the magnet sections 14a and 14b may be flat and/or parallel to the ending plates 45a and 45b.

FIGS. 11a-11b show an example of a magnetic field and a corresponding imaging volume 30 provided by the embodiment of the magnetic resonance imaging system 10 depicted in FIG. 10. In the depicted example, the magnetic field lines are oriented essentially parallelly within the imaging volume 30. FIG. 11b further shows that the magnet sections 14a and 14b may comprise polygonal cross-sections 44. In at least one example embodiment, the cross-section 44 of a magnet 14 or a magnet section 14 comprises a rectangular, a polygonal, an oval, an elliptic or a sickle shape with one or more bends or curvatures. It is also possible, that the cross-section 44 of a magnet 14 or magnet section 14 is continuous or discontinuous and comprises a plurality of solitary or connected elements with any of the shapes mentioned above. In the embodiment depicted in FIG. 11b, the magnet sections 14a and 14b are composed of a multitude of bar magnets or magnet cuboids producing an overall polygonal cross-section 44 with several elements.

However, the embodiment depicted in FIGS. 10 and 11 shall be understood as a mere example of a design of the field generation unit 12. In at least one example embodiment, other types of magnets 14 according to any embodiment described herein are used to provide an imaging volume 30 with high magnetic field homogeneity within the half-open space 47 of the magnetic resonance imaging system 10.

Figure 12:
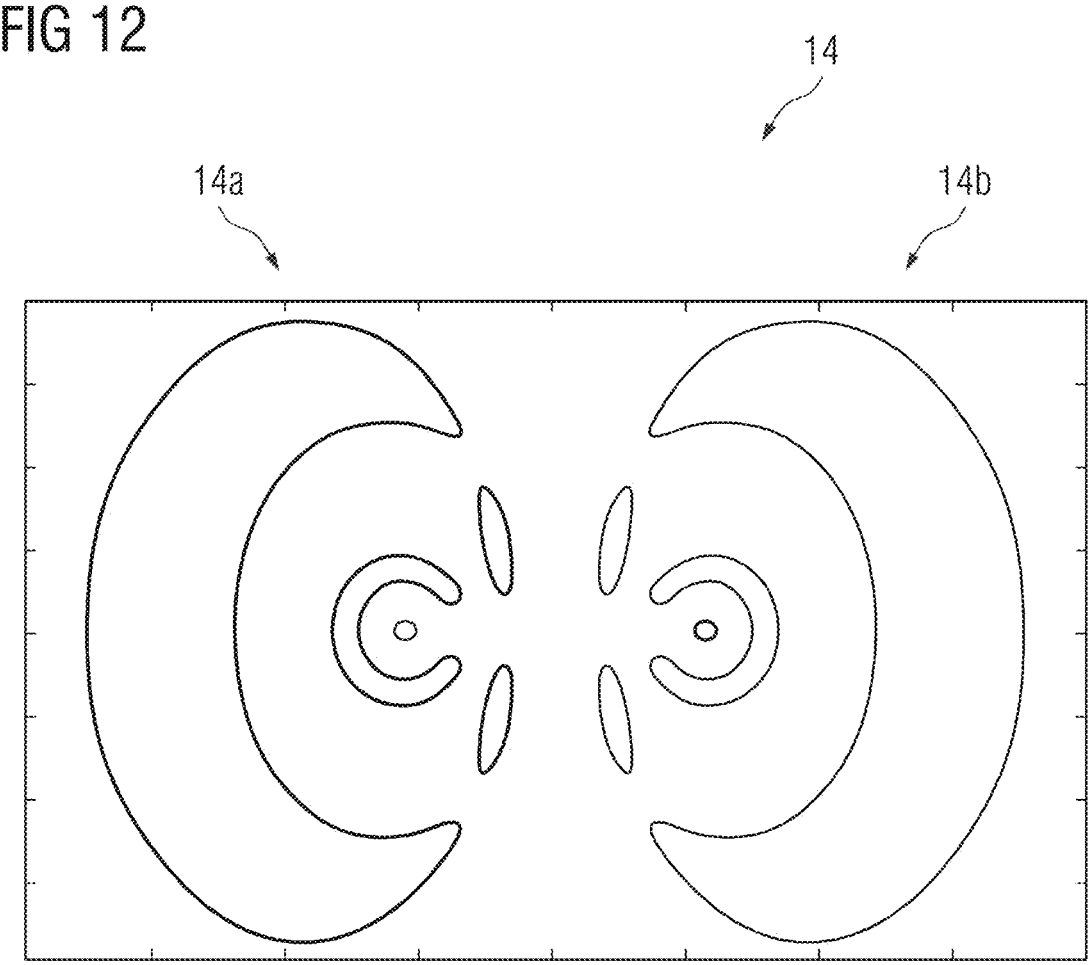
FIG. 12 illustrates a representation of an embodiment of an magnetic resonance imaging system.

Other example embodiments may comprise, for example, low temperature or high temperature superconductors (HTS) as main magnets 14 for the field generation unit 12, but also for the flux return path in the supporting structure 11 and/or yoke 18. The magnetic flux density in the imaging volume 30 may range between 0.1 and 1.5 T. In one embodiment, the magnetic flux density may be higher than 0.2 T and lower than 1 T. In a further embodiment, a target value may be in the range of 0.3 to 0.6 T. A superconducting magnet 14 may comprise coiled wires. However, other example embodiments may be without wires. FIG. 12 shows an embodiment of a winding pattern for a superconducting magnet (B0 magnetic field) with two magnet sections 14a and 14b for the triangular magnetic resonance imaging system 10. The winding patterns of the superconducting magnet 14 are flattened out for an easier understanding of the concept. Analogous to FIG. 10, the left magnet section 14a of the magnet 14 may be carried by a left ending plate 45a of the supporting structure 11 and the right section 14b of the magnet 14 may be carried by a right ending plate 45b of the supporting structure 11. The angle between the magnet sections 14a and 14b may correspond to any of the values given above.

In one embodiment, a complex arrangement of the field generation unit 12 enclosing the half-open space 47 is exploited to shape the imaging volume 30 and provide a B0 magnetic field with well-defined properties (e. g. orientation of magnetic field lines, homogeneity of the magnetic field, etc.). For example, in the embodiment depicted in FIG. 12, the B0 magnetic field may not only be affected by the angle and/or the geometry of the ending plates 45a and 45b carrying the superconducting magnet 14, but also by the winding pattern, as well as an arrangement of the superconducting magnet 14 in a three-dimensional space. Similar considerations apply to permanent magnets or arrays of permanent magnets, which may comprise a complex 3D shape to provide a desired property of the B0 magnetic field. In at least one example embodiment, the field generation unit 12 comprises a 'U' shape or a 'Bell' shape (see FIGS. 19*a*-19*e*), in order to take advantage of the degrees of freedom provided by the 3D arrangement of a magnet 14 or magnet sections 14 enclosing the imaging volume 30. In at least one example embodiment, the design of the gradient field system 27 and/or the radiofrequency system 29 of the magnetic resonance imaging system 10 may be implemented with the same considerations in mind.

As described above, the magnetic resonance imaging system 10 may comprise a gradient field system 27. In the embodiment of the magnetic resonance imaging system 10 shown in FIG. 13, the gradient coils 28*a* and 28*b* of the gradient field system 27 are fully recessed into flat sides oriented in the direction of the imaging volume 30 of conical sections of the magnets 14*a* and 14*b*. An overall shape of the depicted field generation unit 12 corresponds to a 'C' shape (or 'U' shape). In this example, the magnets 14*a* and 14*b* are carried by two ending plates of a yoke 18 acting as a supporting structure 11.

In one embodiment of the magnetic resonance imaging system 10, a gradient coil 28 may be positioned outside of the field generation unit 12 in order to allow for a scale-down of the magnets 14*a* and 14*b*.

According to another embodiment, the gradient field system 27 comprises two gradient coils 28*a* and 28*b* which provide magnetic field gradients in a first direction and in a second direction oriented essentially perpendicular to the first direction. A spatial encoding in a third direction oriented perpendicular to the first direction and the second direction may be accomplished via a static field gradient implemented by the B0 magnetic field (e.g. via a magnet 14 or magnets 14*a* and 14*b*). In at least one example embodiment, a gradient direction coincides with one principal B0 component.

In a further embodiment, the direction of at least one gradient field deviates from an orthogonal alignment with the B0 magnetic field. The at least one magnetic gradient field may thus be oriented in any desired direction. This may facilitate positioning and/or integration of the gradient field system in the magnetic resonance imaging system 10 and increase space efficiency in the half-open space 47 of the field generation unit 12. However, in at least one example embodiment, at least one gradient coil 28 induces a gradient field directed essentially orthogonal to a magnet section 14 and/or an ending plate 45 of the supporting structure 11 as depicted in FIG. 14*b*. In this example, the gradient coils 28 are arranged in a plate-shaped section (e. g. a plate comprising gradient coils 28 or a 'gradient plate') which may be carried by a magnet section 14 and/or an ending plate 45 of the triangular magnetic resonance imaging system 10.

Figure 14A:
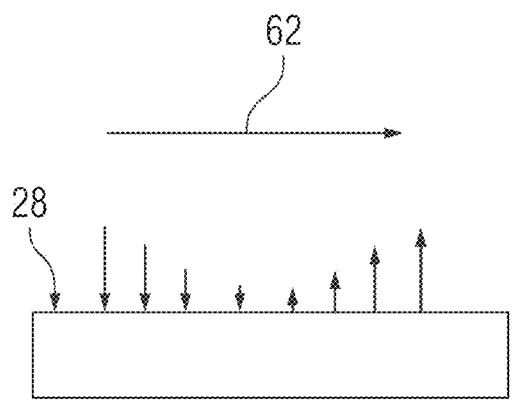
FIGS. 14a-14b illustrate a schematic representation of an embodiment of a gradient field system of a magnetic resonance imaging system.
Figure 14B:
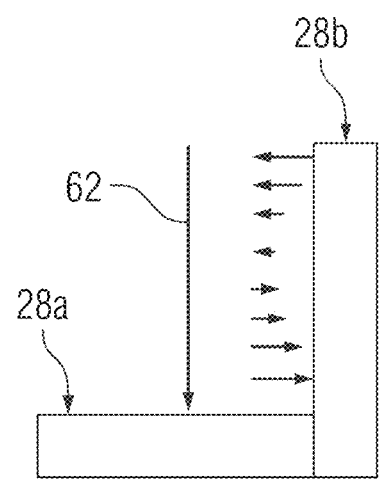

FIG. 14*a* shows an example of how a changing magnetization along a gradient plate 28 may generate a field gradient in one of the directions 62 along the surface of the gradient plate 28. The field gradient may comprise a zero crossing in a center of an anticipated imaging volume 30. In at least one example embodiment, the changing magnetization along the gradient plate 28 is achieved via a spatially changing current distribution along the gradient plate 28. The direction 62 of the magnetic field gradient may correspond to any direction within a gradient plate 28. Based on this principle, two essentially orthogonal gradient field directions may be implemented within a plane parallel to the gradient plate 28.

However, with just one gradient plate 28 it may be difficult to generate a magnetic field gradient in a direction perpendicular to the plane of the respective gradient plate. FIG. 14*b* shows an example of how a second gradient plate 28*b* is exploited to generate a magnetic field gradient essentially perpendicular to a surface of the first gradient plate 28*a*. The field gradient may again comprise a zero crossing in the center of the anticipated imaging volume 30. In one example, the second gradient plate 28*b* may comprise an angle of 90° with respect to the first gradient plate 28*a*. However, as described above, in at least one example embodiment, other angles between the first gradient plate 28*a* and the second gradient plate 28*b* (and thus the first magnet section 14*a* and the second magnet section 14*b*) are implemented. Based on the example embodiments depicted in FIGS. 14*a*-14*b*, the triangular magnetic resonance imaging system 10 may comprise three magnetic field gradients directed along all three spatial dimensions, their respective zero crossings positioned in the center of the imaging volume 30. As described above, one of those magnetic field gradients may be implemented via a static magnetic field. The magnetic field gradient relevant for magnetic resonance imaging is typically referring to the component which is oriented parallel to the direction of the B0 magnetic field. In the example depicted in FIG. 14*b*), this component may be oriented diagonally.

Figure 15C:
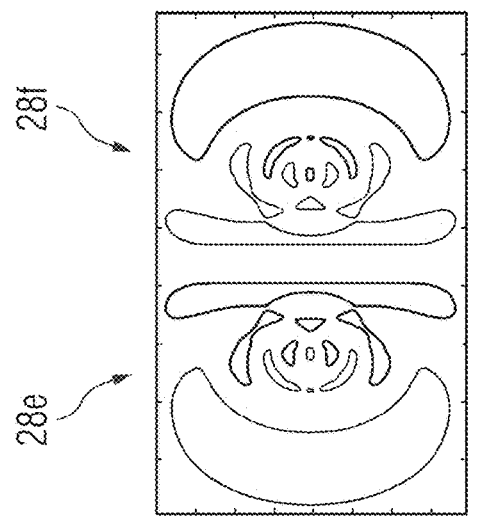
FIGS. 15a-15c illustrate a schematic representation of an embodiment of a gradient field system of a magnetic resonance imaging system.
Figure 15B:
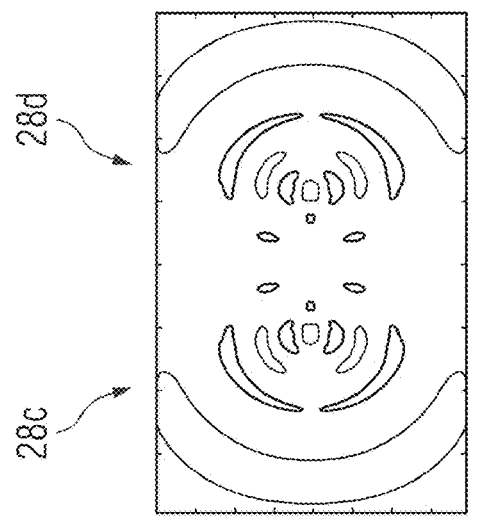
Figure 15A:
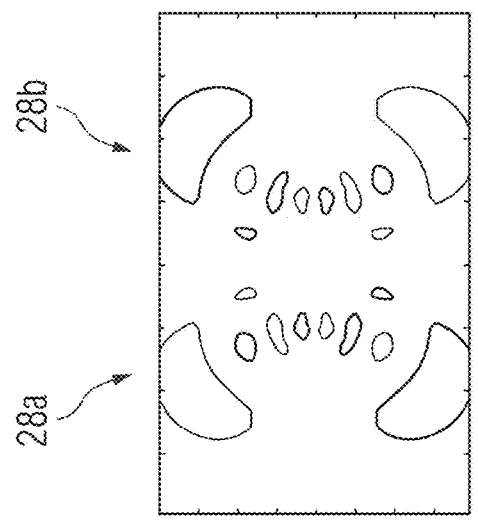

In one embodiment, the gradient field system 27 may comprise superconducting coils. FIGS. 15*a*-15*c* show possible winding patterns of superconducting coils for the magnetic gradient fields in X-, Y- and Z-direction of the magnetic resonance imaging system 10. Analogous to FIG. 12, the winding patterns are flattened out for easier representation and understanding. In one embodiment, the gradient coils 28 are carried by the ending plates 45 of the supporting structure 11. In the depicted example, FIG. 15*a* may correspond to a gradient coil arrangement 28*a* and 28*b* configured to provide a magnetic field gradient in the X-direction, FIG. 15*b* may correspond to a gradient coil arrangement 28*c* and 28*d* configured to provide a magnetic field gradient in the Y-direction and FIG. 15*c* may correspond to a gradient coil arrangement 28*e* and 28*f* configured to provide a magnetic field gradient in the Z-direction.

In one embodiment, the gradient field system 27 may comprise at least two gradient coils, which are inductively decoupled.

Figure 16:
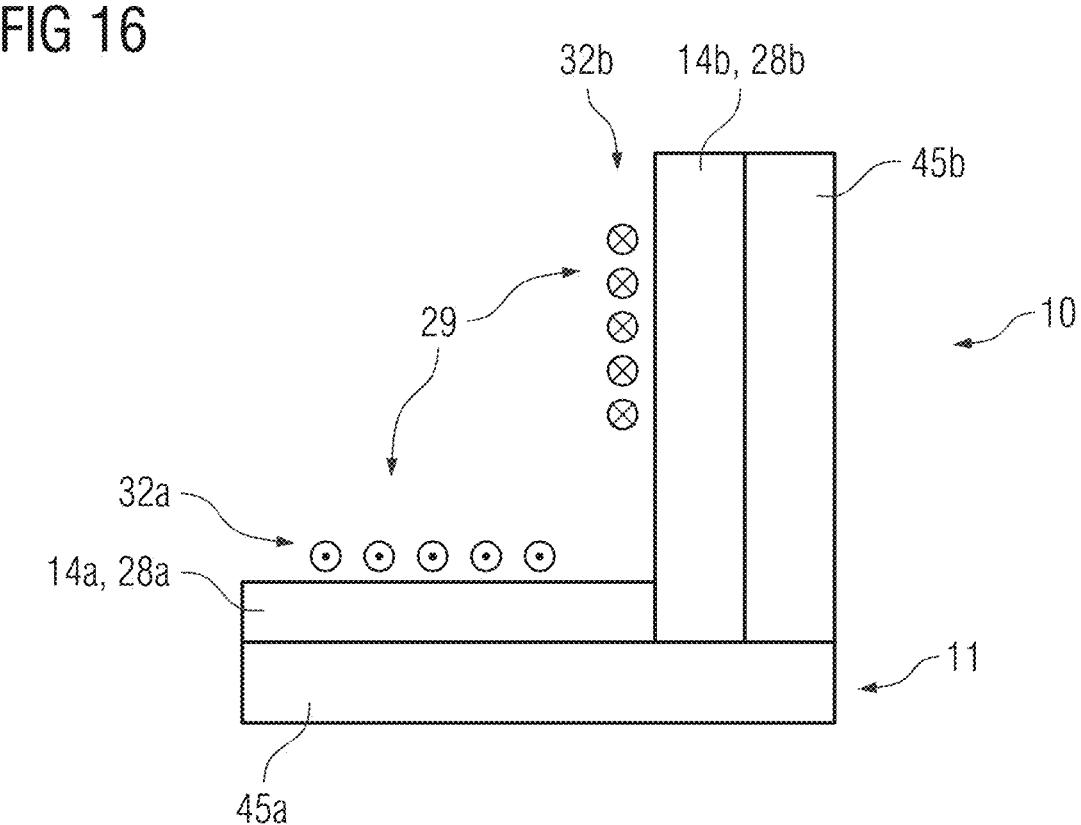
FIG. 16 illustrates a schematic representation of an embodiment of a radiofrequency system of a magnetic resonance imaging system.

The magnetic resonance imaging system 10 may further comprise a radiofrequency system 29. According to one embodiment, the radiofrequency system 29 comprises two radiofrequency antennas 32*a* and 32*b* on either ending plate 45*a* and 45*b* of the supporting structure 11 acting as half resonators: one radiofrequency antenna 32*a* may comprise a 90° phase shift of radiofrequency currents with respect to another radiofrequency antenna 32*b*, thus forming a resonator circuit. The 90° phase shift of radiofrequency currents may be implemented between the two radiofrequency antennas 32*a* and 32*b* on each of the ending plates 45*a* and 45*b* of the supporting structure 11 as depicted in FIG. 16. In this example, radiofrequency currents are applied to rods spanning across the ending plates 45*a* and 45*b* of the supporting structure 11. The rods of one radiofrequency antenna 32*a* on one ending plate 45*a* comprise a 90° phase shift of radiofrequency current with respect to the rods of another radiofrequency antenna 32*b* on the opposing ending plate 45*b*. The term rod may refer to a circular coil, which is squeezed into a rod shape. However, a rod may be a monopole antenna.

Figure 17:
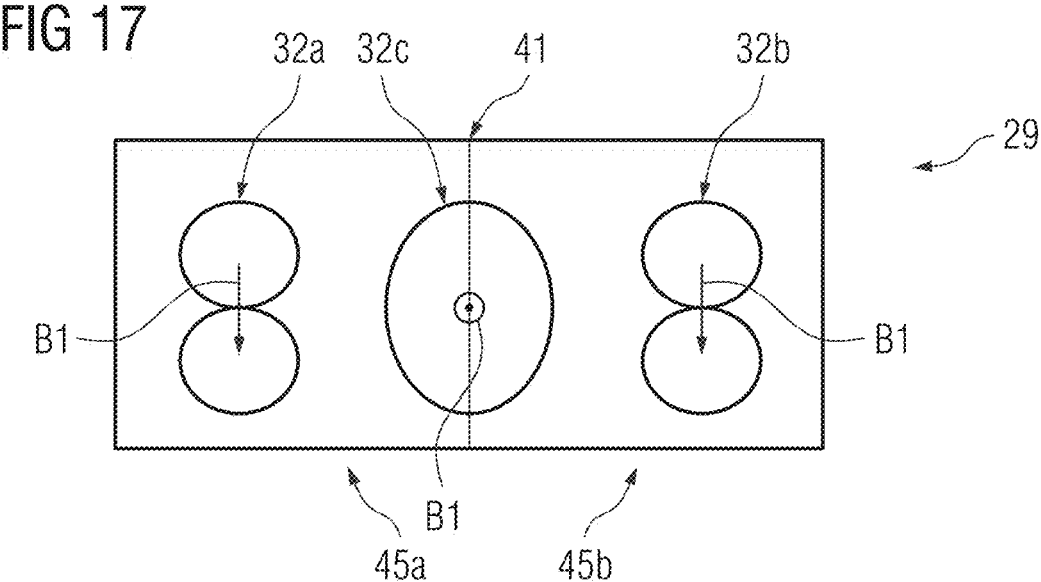
FIG. 17 illustrates a schematic representation of an embodiment of a radiofrequency system of a magnetic resonance imaging system.

According to other embodiments, the at least one radiofrequency antenna 32 (e.g. transmitting antenna) of the radiofrequency system 29 may have the shape of a lemniscate (see FIG. 17). Radiofrequency antennas 32 of this design may be implemented particularly in a triangular magnetic resonance imaging system 10 with a shallow angle and/or narrow half-open space 47 to enhance use of space. However, In at least one example embodiment, the at least one radiofrequency antenna 32 comprises other shapes, as for example a polygonal shape, an oval shape, a shape comprising a plurality of polygons and/or ovals or any other shape that may be obtained by twisting and/or distorting one of the mentioned shapes. The at least one radiofrequency antenna 32 may be positioned between the at least one gradient coil 28 and a protecting cover or cushion to protect the patient 15. In one embodiment, the at least one radiofrequency antenna 32 may provide a linearly polarized B1 magnetic field for the excitation of the spins in a direction parallel to a line along the corner 41 of the triangular magnetic resonance imaging system 10 (e.g. X-direction).

In yet another embodiment, the radiofrequency antenna control unit 22 and/or the radiofrequency system 29 comprises a splitter network 58 as depicted in FIG. 18. The splitter network 58 may be used to weight the amplitudes of the radiofrequency antennas 32*a*, 32*b* and 32*c* (32*a*-*c*) and provide a homogenous and circularly polarized field. The radiofrequency system 29 may comprise three transmitting antennas 32*a*-*c* positioned along the ending plates 45*a* and 45*b* of the supporting structure 11 (or the pole faces 31*a* and 31*b* as shown in FIG. 4*a*), as well as in the corner 41 of the half-open space 47 as depicted in FIG. 17. In at least one example embodiment, the radiofrequency antenna 32*c* positioned in the corner 41 of the half-open space 47 comprises a 90° phase shift with respect to the radiofrequency antennas 32*a* and 32*b*. This may be accomplished using a radiofrequency power amplifier (RFPA) 57 for power supply of the radiofrequency antennas 32*a*-*c* and a splitter network 58 as depicted in FIG. 18. In an example embodiment, radiofrequency antennas 32*a* and 32*b* may comprise a lemniscate-shape, whereas radiofrequency antenna 32*c* may comprise an oval shape overlapping both ending plates 45*a* and 45*b* of the support structure 11 as depicted in FIG. 17 (or overlapping both pole faces 31*a* and 31*b*).

The radiofrequency system 29 may comprise different configurations of radiofrequency antennas 32. In one embodiment, the at least one radiofrequency antenna 32 is capable of both receiving and transmitting radiofrequency signals. In one embodiment, the radiofrequency system 29 may comprise separate receiving and/or transmitting antennas 32. The radiofrequency system 29 may further comprise a multitude of radiofrequency antennas 32, e. g. arranged individually, as an array or as a plurality of arrays.

According to one embodiment, the radiofrequency system 29 may comprise a dedicated radiofrequency system 29 which is designed to match a specific anatomy 60 of a patient 15 (e. g. the head or a shoulder). The radiofrequency system 29 may be carried by the supporting structure 11 and/or the field generation unit 12 of the magnetic resonance imaging system 10. The radiofrequency system 29 may comprise movable parts and/or hinges that may be detached and/or folded open in order to facilitate access of an imaging object to the imaging volume 30 and/or adjust a relative position of the radiofrequency system 29 with respect to the imaging object. The radiofrequency system 29 may prevent and/or reduce movement of the imaging object during an imaging examination. In particular, the radiofrequency system 29 may be designed to at least partially envelope an anatomy 60 of the patient 15 in order to increase coverage of the anatomy and/or enhance homogeneity and circularity of a B1 field.

According to the embodiment depicted in FIG. 19*a*, the radiofrequency system 29 comprises a support element 59 protruding outward from the corner 41 of the half-open space 47, for resting the lower jaw of the patient 15 and prevent movement during an imaging examination. The support element 59 may comprise an essentially horizontal plane as a resting place for the lower jaw of the patient 15. The support element 59 may include an indentation shaped to fit a lower jaw in order to enhance enclosure of the patient 15 anatomy with radiofrequency antennas and/or increase comfort of the patient 15. In a further embodiment, the radiofrequency system 29 may comprise an 'L'-shape as depicted in FIGS. 19 *b*) and *c*) supporting a chin of the patient 15 on a lower (e.g. horizontal) part of the 'L', while limiting movement of the patient 15 against an upper (e.g. vertical) part of the 'L'.

Still further embodiments of the radiofrequency system 29 may comprise a support element 59 that partially or entirely encloses the head of a patient 15 and/or encompass it with flexible or foldable radiofrequency antennas 32 as shown in FIGS. 17 *d*) and *e*). For this purpose, the radiofrequency antenna 32 may be embedded within the support element 59.

In one embodiment, the radiofrequency system 29 is designed to match a contour and/or a surface of the imaging object to enhance coverage of the imaging object and/or decrease a distance between the radiofrequency system 29 and/or a radiofrequency antenna 32 and the surface of the imaging object. The radiofrequency system 29 may also be configured to provide guidance for accessing the imaging volume and/or enhance positioning of the imaging object relative to the imaging volume 30. In an example embodiment, the radiofrequency system 29 may be shaped to fit a head (see FIGS. 19*a*-19*e*), a shoulder, an extremity or other body parts of the patient 15. The radiofrequency system 29 may also be designed to fit a plurality of body regions of a patient 15.

According to one embodiment, the radiofrequency system 29 is configured to carry an auditory system as described above. For example, the auditory system may be integrated into the support element 59 of the radiofrequency system 29. With reference to the embodiments shown in FIGS. 19*d* and 19*e*, the auditory system may be positioned in proximity to an ear of a patient 15 on at least one side of the support element 59 encompassing at least a part of the head of the patient 15.

Figure 20A:
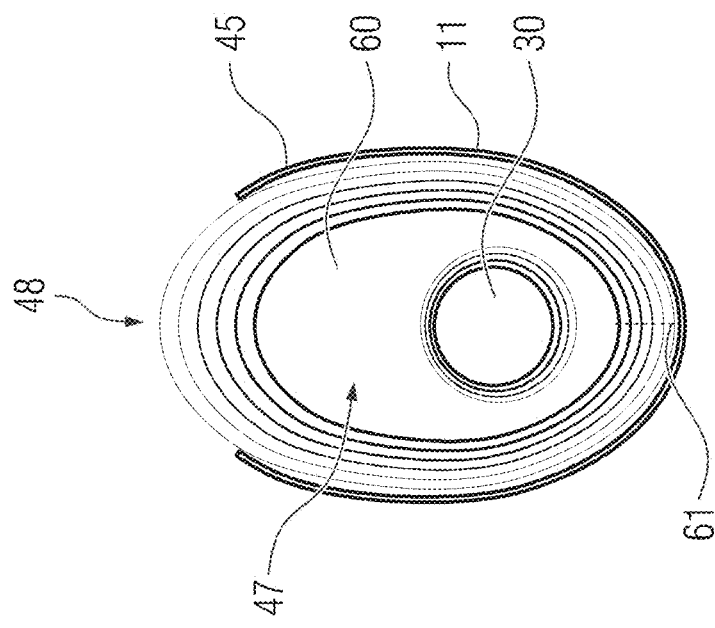
FIGS. 20a-20b illustrate a schematic representation of embodiments of a magnetic resonance imaging system.
Figure 20B:
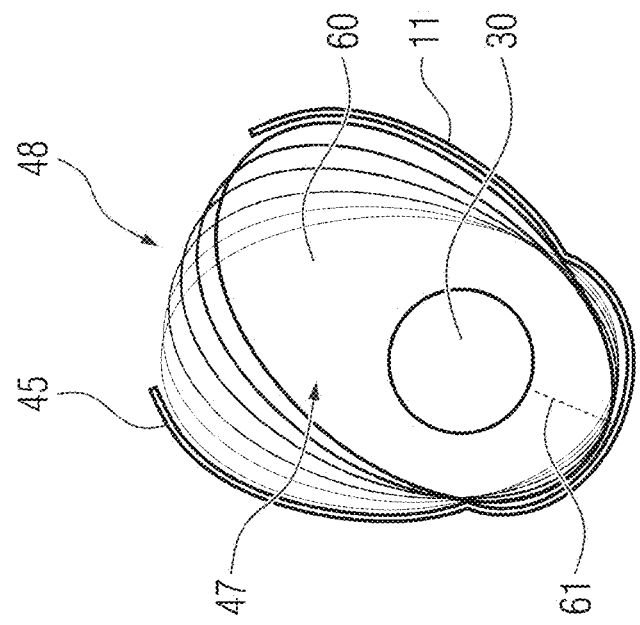

The magnetic resonance imaging system 10 may comprise an opening 48 or gantry designed for enhanced anatomical access. Particularly, a geometry of the opening 48 may be designed to match a shape of an imaging object. In one example, the supporting structure 11 and/or the field generation unit 12 are configured to match at least a part of the contour and/or the surface of an anatomical structure of a patient 15 (e. g. a shoulder or a head) and may also take into account different body positions and/or postures required for the imaging examination. The shape of the opening 48 may compensate for a variance of anatomical sizes, shapes and/or orientations and/or provides an enhanced coverage of the inner anatomical structures to be imaged. FIGS. 20*a*-20*b* shows example variances in size and orientation of an outer contour of an anatomy 60 of a patient 15 positioned in the half-open space 47 of the magnetic resonance imaging system 10. For example, the anatomy 60 may relate to a head, a shoulder, a torso or an extremity of the patient 15. To compensate for the variance of anatomical sizes, shapes and/or orientations depicted in FIGS. 20*a*-20*b*, the magnetic resonance imaging system 10 may particularly comprise a 'U'-shape or a 'Bell'-shape.

In both the 'Bell'-shaped and 'U'-shaped systems, an orientation, a length, a curvature and/or a radius 61 of an ending plate 45 and/or a supporting structure 11 may be designed to facilitate access to the half-open space 47 comprising the imaging volume 30. For example, the access to the half-open space 47 may be predetermined by an angle or a radius 61 in a corner or nook of the half-open space 47. As described above, the ending plates 45 may be movably mounted, e. g. via a hinge or other movable joint, to enable an adjustment of an angle between the ending plates 45. This may faciliate the access to the half-open space 47 and further provide options to customize a shape, a size and/or an orientation of the imaging volume 30 to match a specific medical demand, body region and/or imaging examination.

In particular the 'Bell'-shaped magnetic resonacen imaging system 10 may be adapted to key variance parameters of specific imaging objects or anatomies 60, as the smaller 'U'-section limits its use for imaging a great variety of body parts. Thus, the 'Bell'-shaped system may be matched to specific anatomies 60, such as the head or the shoulders, whereby the relevant anatomy 60 may be closely encompassed by the field generation unit 12 to provide an enhanced coverage of the inner anatomical structures to be imaged.

FIGS. 20*a*-20*b* illustrate the concept of matching a shape of the magnetic resonance imaging system 10 to varying sizes and orientations of a target anatomy 60. In one embodiment, the radius 61 in the corner or nook of the 'U'-shaped or 'Bell'-shaped magnetic resonance imaging system 10 may be tailored to match a human head. For example, the radius of a 'U'-shaped magnetic resonance imaging system 10 may range between 5 cm and 12 cm. The radius 61 of a pediatric magnetic resonance imaging system 10 may range between 5 cm and 8 cm, whereas the radius 61 of a magnetic resonance imaging system 10 for adults ranges between 8 cm and 12 cm. Accordingly, the length of an ending plate 45 may range between 12 cm and 32 cm. The ratio of the radius 61 in the corner of the field generation unit 12 and the length of an ending plate 45 of the magnetic resonance imaging system 10 may range between 0.7 and 0.85.

The concept of compensating for different sizes and/or orientations of an anatomy 60 is of particular importance for a dedicated magnetic resonacen imaging system 10, as it enables a doctor to examine a patient 15 in a position and/or posture that usually cannot be examined in a convential magnetic resonance imaging system 10.

FIGS. 20*a*-20*b* also show different considerations regarding a shape of the ending plates 45 of a 'Bell'-shaped magnetic resonance imaging system 10. A feasible shape of the tips of the ending plates 45 may be derived from considerations regarding the access to the imaging volume 30, geometrical variances of imaging objects, as well as sufficient enclosure of the imaging object in the field generation unit 12. The tips of the ending plates 45 may be tilted inwards towards the imaging object as shown in FIG. 20*a* to provide enhanced coverage of the target anatomy 60. The tips may comprise a more parallel orientation at the opening as depicted in FIG. 20*b*, without enclosing the imaging object at the opening 48 or the gantry. However, the tips of the ending plates 45 may also tilt outwards away from the imaging volume 30, as this shape may provide benefits to a shape and/or orientation of the imaging volume 30, as well as to the shape and/or positioning of a magnet 14 within the field generation unit 12. The shape of the field generation unit 12 may be obtained by incrementally removing or eroding the tips of the ending plates 45 until a required geometry of the opening to the half-open space 47 is achieved.

Figure 21A:
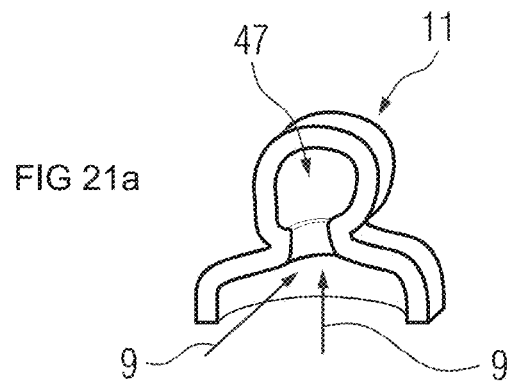
FIGS. 21a-21c illustrate a schematic representation of an embodiment of a magnetic resonance imaging system.
Figure 21B:
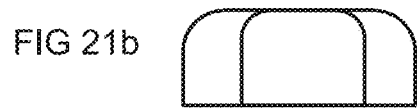
Figure 21C:
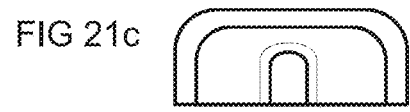

In the embodiment depicted in FIGS. 21*a*-21*c*, the patient 15 may enter the imaging volume 30 in the half-open space 47 along a direction of access 9 from a front side and/or a bottom side of the magnetic resonance imaging system 10. In all other directions, an outer surface of the patient 15 may be covered with magnetic material and/or parts of the supporting structure 11 (e. g. supporting structure 11, yoke 18). In an alternative embodiment depicted in FIGS. 22*a*-22*c*, the direction of access 9 to the imaging volume 30 is implemented from the bottom of the magnet. FIGS. 21*a*-21*c* and 22*a*-22*c* relate to a side view, a top view and a bottom view of the magnetic resonance imaging system 10 respectively.

Figure 22A:
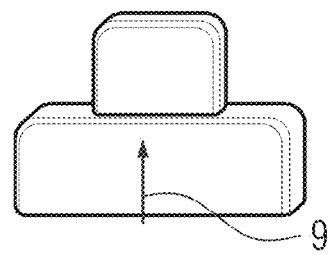
FIGS. 22a-22c illustrate a schematic representation of an embodiment of a magnetic resonance imaging system.
Figure 22B:
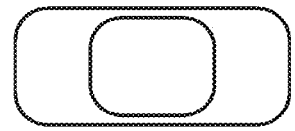
Figure 22C:
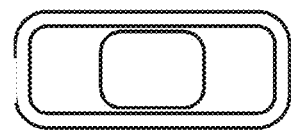

An unobstructed view of the patient 15 may be ensured in example embodiments mentioned above. This may be achieved by provision of a hole 53 or void in the field generation unit 12 (including magnets 14) and/or in parts of the supporting structure 11. A part of a face of the patient 15 may be enclosed with magnetic material and/or radiofrequency antennas 32 in such a way, that the view of the patient 15 is unobstructed. Referring to FIGS. 22*a*-22*c*, a comfort of the patient 15 may be improved by providing holes 53 or voids in a region which is approximately aligned with the eyes and/or the nose of a patient 15 when the patient 15 is positioned within the half-open space 47. However, the magnetic resonance imaging system 10 may comprise a display 49 located in proximity to the eyes, that may be fed with a camera signal from one or more cameras 54 positioned in an examination room and/or in proximity to the magnetic resonance imaging system 10.

In view of the design aspects discussed above, specific embodiments and/or parameters of the magnetic resonance imaging system 10 may be derived, which provide a compromise between requirements related to accessibility of the imaging volume 30, image quality and dedication of the design to specific anatomies 60 and/or anatomical regions. The following examples or embodiments may apply to any of the designs (e. g. triangular shape, 'U' shape or 'Bell' shape) described above.

In one embodiment a size of a free volume in the half-open space 47 is in the same range as a size of the imaging volume 30. For example, a distance of an outer boundary of the imaging volume 30 and a nearest point on a surface of a magnet 14 or magnet section 14 may essentially coincide with a mean diameter (DSV) of the imaging volume 30. The mean diameter of the imaging volume 30 may amount to any of the values described above. In another example, a distance between a center of the imaging volume 30 and the nearest point on the surface of the magnet 14 or magnet section 14 may amount to 1.5-fold the diameter of the imaging volume 30. In one embodiment, a ratio of a length of an ending plate 45 and a diameter of the imaging volume 30 may range between two and eight or, preferably, between three and five. Referring to the embodiment shown in FIG. 2, a length of an ending plate 45*a*, 45*b* may amount to 40 cm and the diameter of the imaging volume is 10 cm, thus providing a ratio of four.

The embodiments described above may comprise any desired magnetic material. Field generation units 12 with permanent magnets may comprise, for example, iron, cobalt, nickel, as well as neodymium, samarium, zirconium, boron and alloys thereof. A grade of the magnetic material may range between a N45 grade and a N52 grade. The magnet 14 may be a single piece or may comprise a plurality of individual pieces or even arrays of smaller magnets with uniform or varying magnetic properties (e. g. magnetic strength, orientation). The pieces of magnets may comprise any desired shape.

A material composition of the field generation unit 12 and other parts of the magnetic resonance imaging system 10 may significantly affect the handling of the magnetic resonance imaging system 10. A specific ratio of a weight of the field generation unit 12 and a capacity of the imaging volume 30 may be between 0.05 kg/cm$^3$ and 0.5 kg/cm$^3$. Magnetic resonance imaging systems with a specific ratio in roughly this range may be used as stationary and/or mobile scanners, allowing for a comparably easy transport and handling without specialized equipment.

As described above, the magnet 14 or a magnet section 14 may also comprise coiled wires made from alloys of niobium, copper, iron, titanium, magnesium, boron and/or tin. The magnet 14 may further comprise low temperature superconductors and/or high temperature superconductors. In one embodiment, the magnet 14 may be a 3D printed magnet 14 comprising a gap, a nook, a hole 53, an indentation, a cut-out and/or a recess in order to provide clearance and/or improve comfort for the patient 15. The 3D printed magnet 14 may further comprise a predetermined distribution of atomic magnets to optimize the magnetic field with respect to spatial constraints of an architecture of the dedicated magnetic resonance imaging system 10.

The pole faces 31a and 31b of the magnet 14 or magnet sections 14 may be planar or non-planar to provide a concise enclosure of an imaging object. For example, a pole face 31 may comprise a conical, a concave or a convex shape to match a desired patient anatomy 60. A gradient coil 28 of the gradient field system 27 may be positioned adjacent to a pole face 31 of the magnet 14 or magnet section 14. The at least one gradient coil 28 and/or the at least one radiofrequency antenna 32 may be at least partially recessed into a pole face 31 to enhance space efficiency of the magnetic resonance imaging system 10. In one embodiment, a magnet 14 of the field generation unit 12 comprises a cylindrical shape, a cone shape, a spherical shape, a cuboid shape or any homeomorphic deformation thereof. The magnet 14 may further comprise a gradient coil 28, which is at least partially recessed into the pole face 31 of the magnet 14 and circumferentially enclosed by the magnet 14 along at least a part of a direction of extension of the gradient coil 28. The magnet 14 comprises a tapering in one direction of extension. For example, the magnet 14 may taper in the direction of the imaging volume 30 (see FIG. 13). In one embodiment, the magnet 14 may comprise a conical shape, which tapers from a 20 cm diameter to a 10 cm diameter in the direction of the imaging volume 30.

Figure 23:
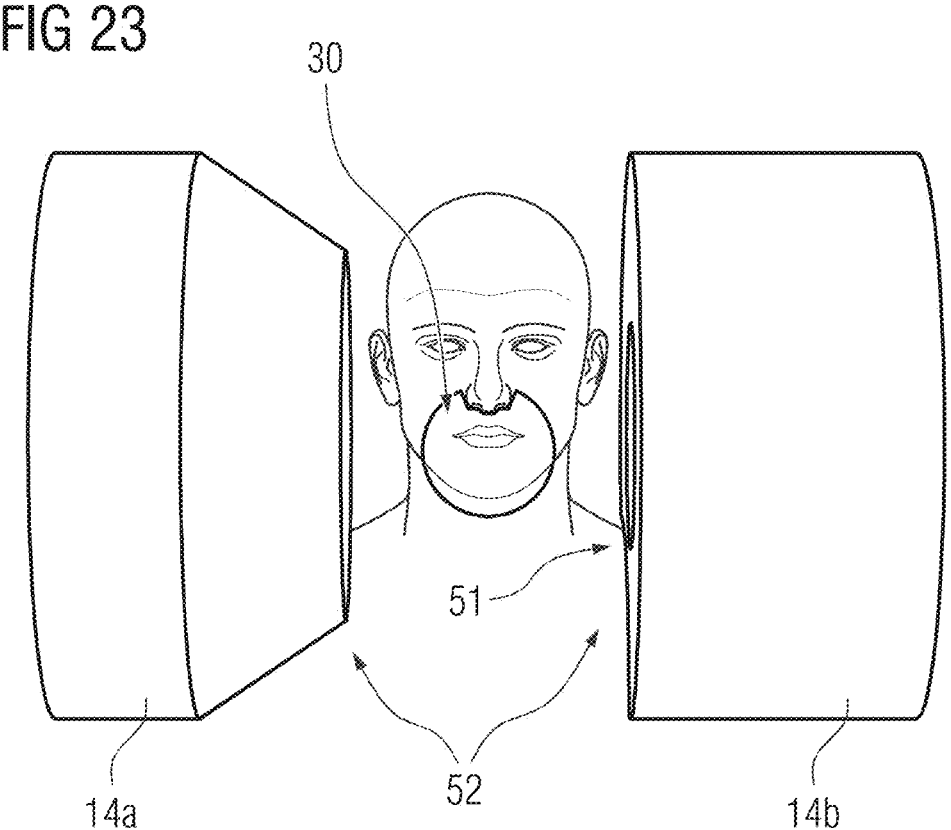
FIG. 23 illustrates a schematic representation of embodiments of a magnetic resonance imaging system.

FIG. 23 shows an arrangement of two magnets 14a and 14b of a simple 'C'-shaped (or 'U'-shaped) magnetic resonance imaging system 10. The cylindrical magnet 14b comprises a cut-out 51 to accommodate the left shoulder of the patient 15. Although the magnet 14a comprises a conical shape, the magnet 14a still collides with the right shoulder of the patient 15 in a collision region 52. In order to provide clearance for the right shoulder of the patient 15, a cut-out or an indentation may be added to the magnet 14a may and/or an inclination of the conical section may be adjusted. For example, the magnets 14a and 14b may comprise circular cut-outs with a radius in the range of 5 to 25 cm. However, other ways of providing clearance for a patient anatomy 60, such as indentations, recesses, voids or curvatures of any shape in the magnets 14a and 14b are possible.

Further design considerations:

According to one embodiment, the magnetic flux density of the magnetic resonance imaging system 10 may range between 0.1 and 1 T. The imaging volume 30 may comprise a maximum diameter of 12 cm. The field generation unit 12 may comprise a triangular shape, a 'U' shape or a 'Bell' shape according to an embodiment described above. In at least one example embodiment, a 5 Gauss line, wherein ferromagnetic objects are prohibited, is located within a radius of 1 to 3 m or 2 to 5 m from the center of the imaging volume 30. The location of the 5 Gauss line may also scale with the imaging volume 30 in a linear or non-linear way.

In one embodiment of the magnetic resonance imaging system 10, the field generation unit 12 is homeomorphic to a half-torus which is cut along a poloidal plane, whereby a cut-out section provides the opening 48 to access the imaging volume 30. In at least one example embodiment, a hole or center of the half-torus comprises the half-open space 47 with the imaging volume 30.

In a further embodiment, the field generation unit 12 of the proposed magnetic resonance imaging system 10 comprises a 'U'-shape (a 'C' is regarded as corresponding to a 'U') or a 'Bell'-shape. The shape of the magnet 14 of the field generation unit 12 may correspond to the overall shape of the magnetic resonance imaging system 10. In one example, a shape of a cross-section of the field generation unit 12 may correspond to the shape of a 'V', a 'U' or a 'Bell'. In at least one example embodiment, the magnet 14 comprises a coiled wire, a high temperature superconductor or a low temperature superconductor.

The field generation unit 12 of the magnetic resonance imaging system 10 may have a symmetrical or an asymmetrical shape. In an asymmetrical configuration the field generation unit 12 may comprise a first magnet 14a and a second magnet 14b. The imaging volume 30 may be located closer to the first magnet 14a, resulting in an asymmetric position of the imaging volume 30 within the half-open space 47. In a symmetrical configuration, the center of the imaging volume 30 may be positioned on a symmetry plane of the field generation unit 12 and comprise an equal distance to the first magnet 14a and the second magnet 14b.

In another embodiment, the field generation unit 12 may comprise a symmetry in two planes and the center of the imaging volume 30 may be positioned along an intersection between the two planes (see FIG. 3). In a simple example, the field generation unit 12 may comprise permanent magnets with circular or elliptical pole faces, or any other geometry derived by extending and/or distorting a circular pole face in one direction.

The field generation unit 12 may further comprise pole rings (or pole cylinders) that are matched to the shape of a patient anatomy 60 to provide an improved access to the imaging volume 30 and/or enhance enclosure of the anatomy 60 with magnetic material. A matched shape may be any shape that imitates or approximates a contour and/or a surface of an imaging object in two or more dimensions. In one example, the field generation unit 12 may provide an extra cavity for a shoulder of the patient 15 (see FIG. 23). In at least one example embodiment, a magnet 14, the supporting structure 11 and/or the field generation unit 12 is specifically shaped in dependence of key variance factors of an imaging object, such as the head or the shoulder of a patient 15 (see FIGS. 20a-20b).

According to a further embodiment, the magnetic resonance imaging system 10 provides a recess, a cut out, a void and/or 3D curvature in the supporting structure 11 and/or the field generation unit 12. For this purpose, features like the diameter, shape, and orientation of the at least one magnet 14, as well as a relative position of magnets 14 and/or magnet sections 14 may be adapted to provide clearance for a patient anatomy 60 (e. g. the shoulders of the patient 15) and enhance positioning of the target anatomy 60 in the imaging volume 30. In at least one example embodiment, 3D printed magnets may be used, particularly 3D printed high temperature superconductors, to provide complex magnet shapes. The field generation unit 12 may also comprise arrays of magnets 14, e. g. Hallbach arrays, with dedicated arrangements of individual magnets and magnetic orientations. In some embodiments, coiled wires may be routed around a recess for an anatomy 60 or a permanent magnet may be cut to provide a desired shape (see FIGS. 4a-4).

Based on a variation of orientations and sizes of a target anatomy 60 in all required directions, a 3D shape of the field generation unit 12 may be derived, that encloses at least a part of the imaging volume 30 as well as a part of the outer surface of a relevant anatomy 60 (see FIGS. 20 to 23).

As a further design aspect, mechanical forces such as weight forces and magnetic forces may be considered and may in some instances dominate the design of the supporting structure 11. In one embodiment, the design of the magnet is based on a multi-dimensional optimization, taking into account at least
a desired openness (e.g. sufficient view angle of a patient 15) and the accessibility of the half-open space 47, a mechanical force involved in handling and operating the magnetic resonance imaging system 10,
a magnetic force of the field generation unit 12 and the gradient field system 27,
a coverage of the imaging object's outer boundaries with magnet material (e.g. active poles, iron yoke) to maximize field efficiency and/or homogeneity.

The embodiments described above are to be recognized as examples. Individual embodiments may be extended by features of other embodiments.

We claim:

1. A magnetic resonance imaging system comprising:
a field generation unit including at least two magnet sections configured to generate a B0 magnetic field, the at least two magnet sections having an angle between each other to form a triangular half-open space that encloses at least a part of an imaging volume within the B0 magnetic field, the imaging volume being configured to be accessed via an open space of the triangular half-open space in at least one spatial directions at an angle form a main direction of magnetic field lines of the B0 magnetic field in the imaging volume;
a support structure to structurally support the field generation unit;
a radiofrequency system including at least one radiofrequency antenna configured to at least one of transmit radiofrequency radiation or receive radiofrequency radiation; and
a gradient field system including at least one gradient coil to generate at least one magnetic gradient field.

2. The magnetic resonance imaging system according to claim 1, wherein
the field generation unit encompasses the imaging volume such that the field generation unit at least partially encompasses a free volume, and
a ratio between a volume of the imaging volume and a volume of the free volume is between 0.05 and 1.

3. The magnetic resonance imaging system according to claim 2, wherein the field generation unit matches at least one of a part of a contour of an imaging object or a surface of the imaging object to increase a coverage of the imaging object.

4. The magnetic resonance imaging system according to claim 1, wherein the at least two magnet sections include a permanent magnet or an array of permanent magnets.

5. The magnetic resonance imaging system according to claim 1, wherein the at least two magnet sections include at least one of high temperature superconducting materials or low temperature superconducting materials.

6. The magnetic resonance imaging system according to claim 1, wherein the support structure at least one of is movably mounted or includes a positioning unit configured to adjust at least one of a position of the field generation unit with respect to an imaging object or the at least one spatial direction to access to the imaging volume.

7. The magnetic resonance imaging system according to claim 1, wherein a shape of the support structure matches at least one of a contour of an imaging object or a surface of the imaging object to increase a coverage of the imaging object.

8. The magnetic resonance imaging system according to claim 1, wherein
the gradient field system includes two gradient coils to generate a first magnetic field gradient in a first direction and a second magnetic field gradient in a second direction perpendicular to the first direction, and
the magnetic resonance imaging system is configured to spatially encode in a third direction perpendicular to the first direction and the second direction via a static field gradient from the B0 magnetic field.

9. The magnetic resonance imaging system according to claim 1, wherein the radiofrequency system matches at least one of a contour of an imaging object or a surface of the imaging object to at least one of increase a coverage of the imaging object or decrease a distance between the at least one radiofrequency antenna and the surface of the imaging object.

10. The magnetic resonance imaging system according to claim 1, wherein
the field generation unit includes at least one symmetry plane, and
the at least one spatial direction is perpendicular to the main direction of magnetic field lines of the B0 magnetic field in the imaging volume and parallel to the at least one symmetry plane.

11. The magnetic resonance imaging system according to claim 1, wherein the field generation unit includes two symmetry planes.

12. The magnetic resonance imaging system according to claim 1, wherein a cross-section of at least one of the field generation unit or the support structure is a 'U', a 'C', or a bell shape.

13. The magnetic resonance imaging system according to claim 1, wherein
the at least one spatial direction includes a first spatial direction to access the imaging volume and a second spatial direction to access the imaging volume, and
the first spatial direction is perpendicular to the second spatial direction.

14. The magnetic resonance imaging system according to claim 1, wherein
the support structure includes two ending plates configured to carry the at least two magnet sections, and the two ending plates are in alignment with the triangular half-open space.

15. The magnetic resonance imaging system according to claim 14, wherein
the radiofrequency system includes at least two radiofrequency antennas, and
at least one of the two ending plates is configured to carry at least one radiofrequency antenna of the at least two radiofrequency antennas.

16. The magnetic resonance imaging system according to claim 15, wherein the at least two radiofrequency antennas include at least one first radiofrequency antenna and at least one second radiofrequency antenna, the at least one first radiofrequency antenna having first radiofrequency currents in a first phase and the at least one second radiofrequency antenna having second radiofrequency currents in a second phase, and
the first phase has a 90° phase shift with respect to the second phase.

17. The magnetic resonance imaging system according to claim 15, wherein
the at least two radiofrequency antennas includes at least one radiofrequency antenna having a coil of wire, and
a shape of the coil of wire is
a lemniscate shape,
an oval shape,
a polygonal shape,
a shape including at least one of a plurality of polygons or a plurality of ovals,
at least one of a twisted polygon shape or a distorted polygon shape, or
at least one of a twisted oval shape or a distorted oval shape.

18. The magnetic resonance imaging system according to claim 15, wherein
the radiofrequency system includes at least one third radiofrequency antenna, in a corner of the triangular half-open space between the two ending plates of the support structure, and
the at least one third radiofrequency antenna has third radiofrequency currents that have a 90° phase shift with respect to radiofrequency currents of at least one of the at least two radiofrequency antennas.

19. The magnetic resonance imaging system according to claim 18, wherein the radiofrequency system includes a splitter network configured to weight an amplitude of the radiofrequency radiation from each of the at least two radiofrequency antennas to generate at least one of a homogenous and circularly polarized B1 magnetic field or a linearly polarized B1 magnetic field.

20. The magnetic resonance imaging system according to claim 1, wherein the angle between the at least two magnet sections is between 10 degrees and 180 degrees.

21. The magnetic resonance imaging system according to claim 1, wherein the at least one gradient coil is at least partially in a recess of at least one magnet section of the at least two magnet sections.

22. The magnetic resonance imaging system according to claim 1, wherein a shape of the imaging volume includes a variability of the B0 magnetic field and the variability of the B0 magnetic field is such that the shape of the imaging volume is non-spherical.

23. The magnetic resonance imaging system according to claim 1, wherein a maximum diameter of a sphere with a same volume as the imaging volume is in a range of 2 cm to 10 cm.

24. The magnetic resonance imaging system according to claim 1, wherein
the imaging volume is configured to be accessed via the open space of the triangular half-open space in a unilateral direction, and
the unilateral direction is an angle with respect to the main direction of magnetic field lines of the B0 magnetic field in the imaging volume.

25. The magnetic resonance imaging system according to claim 1, wherein
the imaging volume is configured be accessed at least two perpendicular spatial directions, and
each of the at least two perpendicular spatial directions is at an angle with respect to the main direction of magnetic field lines of the B0 magnetic field in the imaging volume.

* * * * *